(12) United States Patent
Takeyoshi et al.

(10) Patent No.: US 10,668,153 B2
(45) Date of Patent: Jun. 2, 2020

(54) BORON NEUTRON CAPTURE THERAPY SYSTEM

(71) Applicants: Fujidenolo Co. Ltd., Komaki-shi, Aichi (JP); Cancer Intelligence Care Systems, Inc., Koto-ku, Tokyo (JP)

(72) Inventors: Tsuyako Takeyoshi, Tokyo (JP); Masaru Nakamura, Tokyo (JP); Yoshio Imahori, Tokyo (JP); Hideki Miyazaki, Komaki (JP); Toshitaka Fujioka, Komaki (JP); Shinsuke Kato, Komaki (JP)

(73) Assignees: Fujidenolo Co. Ltd., Komaki-shi, Aichi (JP); Cancer Intelligence Care Systems, Inc., Tokyo (JP)

( * ) Notice: Subject to any disclaimer, the term of this patent is extended or adjusted under 35 U.S.C. 154(b) by 46 days.

(21) Appl. No.: 16/040,172

(22) Filed: Jul. 19, 2018

(65) Prior Publication Data
US 2018/0318420 A1 Nov. 8, 2018

Related U.S. Application Data

(63) Continuation-in-part of application No. PCT/JP2016/051544, filed on Jan. 20, 2016.

(51) Int. Cl.
*A61K 41/00* (2020.01)
*A61N 5/10* (2006.01)

(52) U.S. Cl.
CPC ........ *A61K 41/0095* (2013.01); *A61N 5/1049* (2013.01); *A61N 5/1069* (2013.01);
(Continued)

(58) Field of Classification Search
CPC .............. A61K 41/0095; A61N 5/1049; A61N 5/1051; A61N 5/1064
(Continued)

(56) References Cited

U.S. PATENT DOCUMENTS 5,433,693 A * 7/1995 Ott .......................... A61N 5/10
600/1
5,515,341 A 5/1996 Toda et al.
(Continued)

FOREIGN PATENT DOCUMENTS

CN 1894577 A 1/2007
CN 101022851 A 8/2007
(Continued)

OTHER PUBLICATIONS

English translation of International Preliminary Report on Patentability of PCT/JP2016/051544 dated Jul. 24, 2018.
(Continued)

*Primary Examiner* — Jason L McCormack
(74) *Attorney, Agent, or Firm* — Muncy, Geissler, Olds & Lowe, P.C.

(57) ABSTRACT

A boron neutron capture therapy system has a neutron beam irradiation device, a patient restraint/placement portion, a three-dimensional diagnostic device, an irradiation table, a position adjustment mechanism, and a control unit. The boron neutron capture therapy system performs position determination with a sufficient degree of accuracy at the time of the boron neutron capture therapy. Further, the control unit, using the movement of the irradiation table, performs collision avoidance processing that changes the movement of the irradiation table before the patient restrained on the patient restraint/placement portion receives injury by colliding with the irradiation port, and thus, collision between the patient and the irradiation port can be avoided.

12 Claims, 23 Drawing Sheets

(52) U.S. Cl.
CPC .......... *A61N 5/1077* (2013.01); *A61N 5/1001* (2013.01); *A61N 2005/109* (2013.01); *A61N 2005/1059* (2013.01); *A61N 2005/1061* (2013.01)

(58) Field of Classification Search
USPC ...................................................... 250/492.1
See application file for complete search history.

(56) References Cited

U.S. PATENT DOCUMENTS

| | | | |
|---|---|---|---|
| 5,882,330 A * | 3/1999 | Lemelson | A61K 41/0095 424/450 |
| 2005/0281374 A1 | 12/2005 | Cheng et al. | |
| 2006/0017022 A1 | 1/2006 | Rigney | |
| 2007/0164230 A1 | 7/2007 | Rigney | |
| 2008/0089483 A1 | 4/2008 | Nivestedt et al. | |
| 2008/0187097 A1 * | 8/2008 | Cheng | A61N 5/107 378/65 |
| 2010/0208045 A1 | 8/2010 | Willmann | |
| 2011/0249088 A1 | 10/2011 | Ross et al. | |
| 2013/0342666 A1 | 12/2013 | Willmann et al. | |

FOREIGN PATENT DOCUMENTS

| | | |
|---|---|---|
| CN | 101505710 A | 8/2009 |
| CN | 201788041 U | 4/2011 |
| CN | 105268119 A | 1/2016 |
| EP | 0642843 A1 | 3/1995 |
| EP | 2377576 A1 | 10/2011 |
| JP | S62-204769 A | 9/1987 |
| JP | H07-163670 A | 6/1995 |
| JP | 2012-105746 A | 6/2012 |
| JP | 2015-231497 A | 12/2015 |
| WO | 2005/018734 A2 | 3/2005 |
| WO | 2005018734 A2 | 3/2005 |
| WO | 2015/137251 A1 | 9/2015 |

OTHER PUBLICATIONS

English translation of International Search Report of International Application No. PCT/JP2016/051544 dated Mar. 3, 2016.
The extended European search report for EP application No. 16886294.4 dated Aug. 30, 2019.
Office Action of corresponding Chinese Application No. 201680079478.5 dated Dec. 3, 2019 and English translation thereof.

* cited by examiner

FIG. 11

| AXIS | AUTOMATIC MODE [mm/sec] | MANUAL MODE CONTINUOUS OPERATION [mm/sec] | MANUAL MODE JOG OPERATION [mm/step] |
|---|---|---|---|
| X | 10 | 0.5 | 0.1 |
| Y | 10 | 0.5 | 0.1 |
| Z1 | 9.6@Z200(4~18) DURING MOVEMENT 6@Z0 | 0.48 (0.2~0.9) | 0.08 (0.03~0.15) |
| P | 0.5deg/sec | 0.2deg/sec | 0.1deg/sec |
| R | 1.0deg/sec | 0.2deg/sec | 0.1deg/sec |

FIG. 12

| AXIS | AUTOMATIC MODE [Hz] | MANUAL MODE CONTINUOUS OPERATION [Hz] | MANUAL MODE JOG OPERATION [Hz] |
|---|---|---|---|
| X | 35997 | 3600 | 720 |
| Y1<br>Y2 | 35997<br>35997 | 3600<br>3600 | 720<br>720 |
| Z1<br>Z2 | 4440,<br>(DURING MOVEMENT 1480)<br>28440,<br>(DURING MOVEMENT 9480) | 222<br>1422 | 37<br>237 |
| P | 8265 | 3306 | 1653 |
| R | 3330 | 666 | 333 |

BORON NEUTRON CAPTURE THERAPY SYSTEM

CROSS-REFERENCE TO RELATED APPLICATION

This application is a continuation-in-part of International Application No. PCT/JP2016/051544, filed Jan. 20, 2016. This disclosure of the foregoing application is hereby incorporated by reference in its entirety.

BACKGROUND

The present invention relates to a boron neutron capture therapy system in which treatment is performed by irradiating neutron beams onto an affected part of a patient or a wide area including the affected part, into which boron compounds have been injected A stretcher is known that is provided with a patient placement unit on which the patient is positioned, and a conveyance device that conveys the patient placement unit. With respect to the stretcher, there are cases in which, once the patient placement unit on which the patient has been positioned has been conveyed by the conveyance device, the patient placement unit is moved to another location from the conveyance device. Technology is proposed to make this type of movement simple. One example of this is a slide mechanism of the placement unit of the stretcher or the like, as disclosed in Japanese Patent Application Publication No. JP-A-2012-105746, for example. According to this technology, after moving the placement unit close to a bed using the conveyance device, the placement unit can be easily move to a center portion of the bed using the slide mechanism.

Further, in Japanese Patent Application Publication No. JP-A-2015-231497, a boron neutron capture therapy system used in the treatment of cancer and the like using neutron beams is disclosed. In this boron neutron capture therapy system, a relative positional relationship between a device that irradiates the neutron beams and the body of the patient has an impact on the determination of a section to be treated, and thus, a high degree of positioning accuracy is required. Further, the affected part of the patient that is a treatment target is caused to be as close as possible to an irradiation port of the neutron beams.

SUMMARY

However, in the invention disclosed in Japanese Patent Application Publication No. JP-A-2015-231497, since the affected part of the patient is caused to be as close as possible to the irradiation port of the neutron beams, there is an issue that contact between the patient and the irradiation port must be prevented.

An object of the present invention is to provide a boron neutron capture therapy system capable of performing positioning with sufficient accuracy at a time of boron neutron capture therapy and capable of preventing contact between a patient and an irradiation port.

A boron neutron capture therapy system according to a first aspect of the present invention is provided with a neutron beam irradiation device inside a room covered with neutron beam shielding, and performs treatment by irradiating neutron beams onto an affected part, into which boron compounds have been injected, of a patient, using the neutron beam irradiation device. The boron neutron capture therapy system includes: a patient restraint/placement portion that restrains the patient in a state of being placed on the patient restraint/placement portion; a three-dimensional diagnostic device that detects a position of the affected part in the patient; an irradiation table whose position is determined with respect to the neutron beam irradiation device; a position adjustment mechanism that changes a position of the irradiation table with respect to an irradiation port of the neutron beam irradiation device, in relation to each of directions of three axes that are mutually orthogonal; and a control unit that aligns a position of the affected part in the patient detected by the three-dimensional diagnostic device with a position of neutron beams irradiated from the neutron beam irradiation device by changing, using the position adjustment mechanism, a position relating to each of the directions of the three axes of the irradiation table onto which the patient restraint/placement portion has been transferred, and moves the affected part as close as possible to the irradiation port. The control unit, using movement of the irradiation table, performs collision avoidance processing that changes the movement of the irradiation table before the patient restrained on the patient restraint/placement portion receives injury by colliding with the irradiation port.

According to the first aspect of the present invention, since the boron neutron capture therapy system is provided with the patient restraint/placement portion that restrains the patient in the state of being placed on the patient restraint/placement portion, the three-dimensional diagnostic device that detects the position of the affected part in the patient, the irradiation table whose position is determined with respect to the neutron beam irradiation device, the position adjustment mechanism that changes the position of the irradiation table with respect to the irradiation port of the neutron beam irradiation device in relation to each of the directions of the three axes that are mutually orthogonal, and the control unit that aligns the position of the affected part in the patient detected by the three-dimensional diagnostic device with the position of the neutron beams irradiated from the neutron beam irradiation device by changing, using the position adjustment mechanism, the position relating to each of the directions of the three axes of the irradiation table onto which the patient restraint/placement portion has been transferred, and that moves the affected part as close as possible to the irradiation port, specific requirements of the boron neutron capture therapy system can be sufficiently fulfilled. Specifically, the boron neutron capture therapy system can be provided that performs position determination with a sufficient degree of accuracy at the time of the boron neutron capture therapy. Further, the control unit, using the movement of the irradiation table, performs collision avoidance processing that changes the movement of the irradiation table before the patient restrained on the patient restraint/placement portion receives injury by colliding with the irradiation port, and thus, collision between the patient and the irradiation port can be avoided.

BRIEF DESCRIPTION OF THE DRAWING

Embodiments of the disclosure will be described below in detail with reference to the accompanying drawings in which:

FIG. 11 is a diagram illustrating a movement speed of each of portions relating to positional adjustment of the irradiation table shown in FIG. 3.

FIG. 12 is a diagram illustrating a number of pulses of each of the portions relating to the positional adjustment of the irradiation table shown in FIG. 3.

DETAILED DESCRIPTION OF EMBODIMENTS

Figure 1:
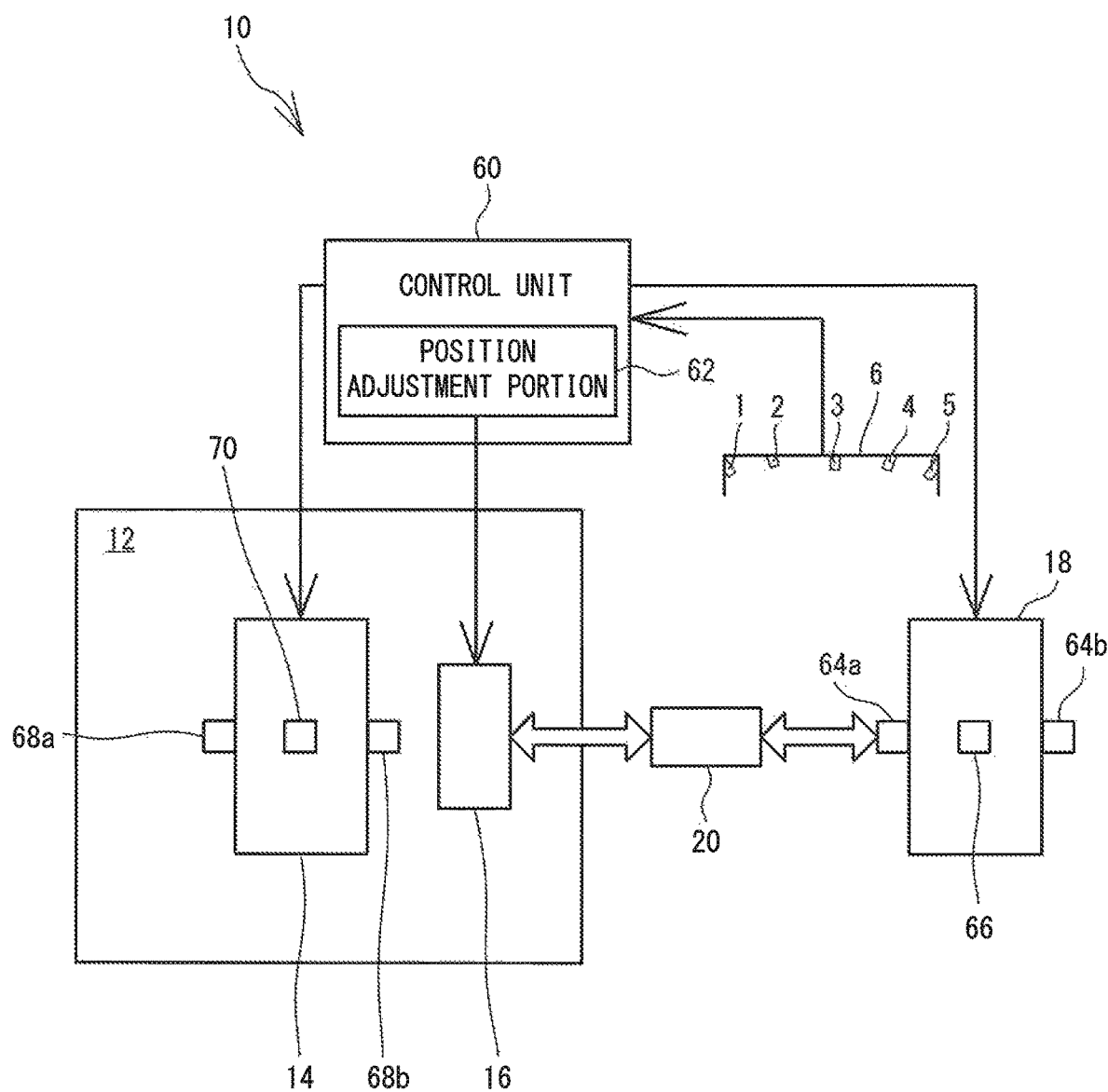
FIG. 1 is a diagram schematically showing an example of a configuration of a boron neutron capture therapy system that is a preferable embodiment of the present invention.

Below, preferred embodiments of the present invention will be described with reference to the drawings. In the drawings used in the following description, proportions and the like of each of parts are not necessarily accurately drawn.

FIG. 1 is a diagram schematically showing an example of a configuration of a boron neutron capture therapy system 10 (hereinafter referred to simply as a therapy system 10) that is a preferred embodiment of the present invention. As shown in FIG. 1, the therapy system 10 of the present embodiment is provided with a neutron beam irradiation device 14 and an irradiation table 16, inside a room 12 that is covered by a neutron beam shielding wall. A three-dimensional diagnostic device 18 is provided outside the room 12. A conveyance device 20 is provided that can move inside and outside the room 12. Further, the therapy system 10 is provided with a camera 1, a camera 2, a camera 3, a camera 4, and a camera 5 supported by an aluminum camera frame 6. The cameras 1 to 5 capture an image, from above, of a patient 8 restrained on a patient restraint/placement portion 22 to be described later, and are used to acquire three-dimensional data of a contour of a body surface.

The therapy system 10 performs therapy by irradiating neutron beams onto an affected part, or a wider area including the affected part, of the patient 8 (refer to FIG. 2 and the like), using the neutron beam irradiation device 14. The neutron beam irradiation device 14 is, for example, a known device that irradiates the neutron beams onto the patient 8 vertically from above, or in the horizontal direction, or the like. In the treatment using the therapy system 10, for example, boron compounds are injected in advance into the body of the patient 8 who is the target of the treatment. After a fixed time period in which the boron accumulates in the affected part, by irradiating the neutron beams from the neutron beam irradiation device 14 onto the affected part or a wider area including the affected part, the neutron beams are captured by the boron. The treatment of a tumor and the like in the patient 8 is performed as a result of alpha rays and the like that are emitted from the boron that has captured the neutron beams. Specifically, the therapy system 10 of the present embodiment performs known boron neutron capture therapy by irradiating the neutron beams onto the affected part of the patient 8 using the neutron beam irradiation device 14.

In the treatment using the therapy system 10, before the neutron beams are irradiated onto the patient 8 by the neutron beam irradiation device 14, the position of the affected part in the patient 8 is detected by the three-dimensional diagnostic device 18. The three-dimensional diagnostic device 18 is a device that captures an image of the inside of the body of the patient 8, and, preferably, is a known X-ray computer tomography (CT) device that irradiates X-rays from many directions onto the body of the patient 8, detects the X-rays that have passed through the body using an X-ray detector, performs computer processing on information of the amount of X-rays that have passed through the body, and re-configures the information as a three-dimensional image. The three-dimensional diagnostic device 18 may be a known magnetic resonance imaging (MRI) device.

Figure 2:
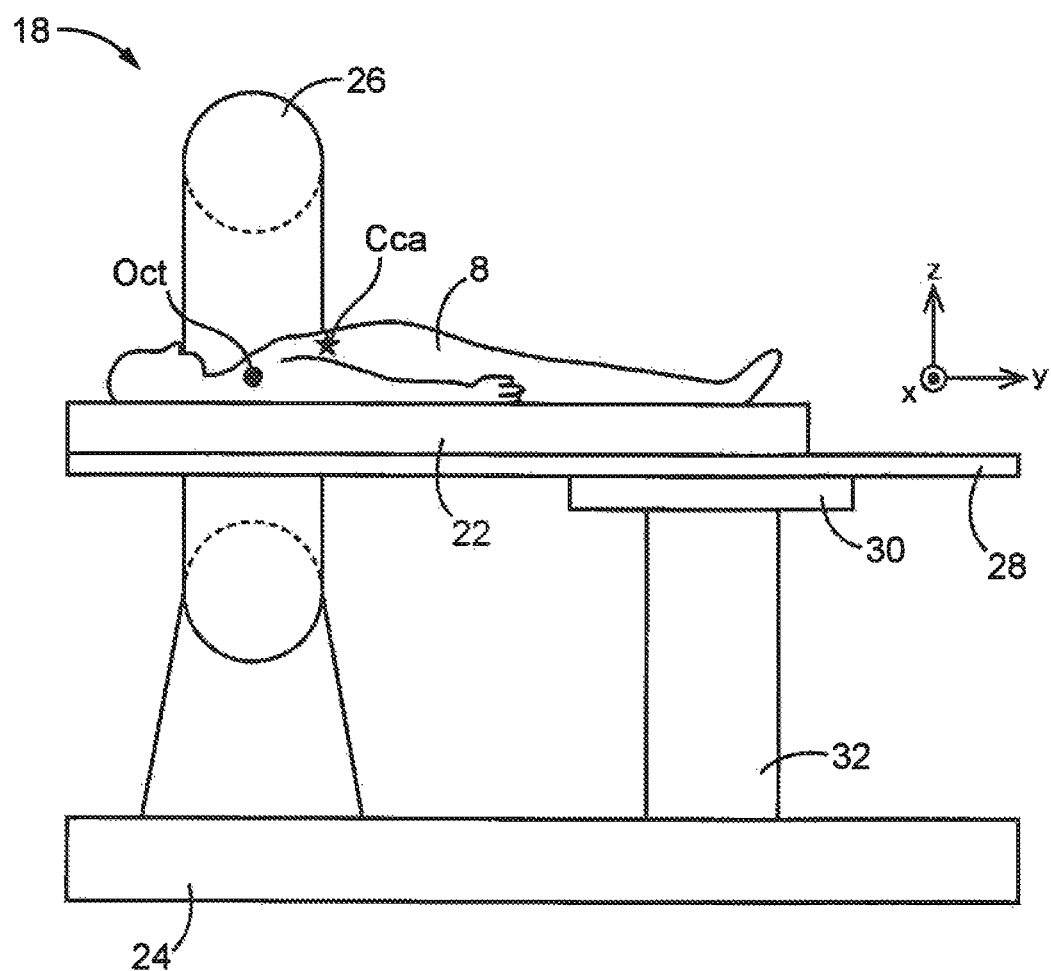
FIG. 2 is a diagram schematically showing a state in which a position of an affected part in a patient is detected by a three-dimensional diagnostic device provided in the therapy system shown in FIG. 1.
Figure 4:
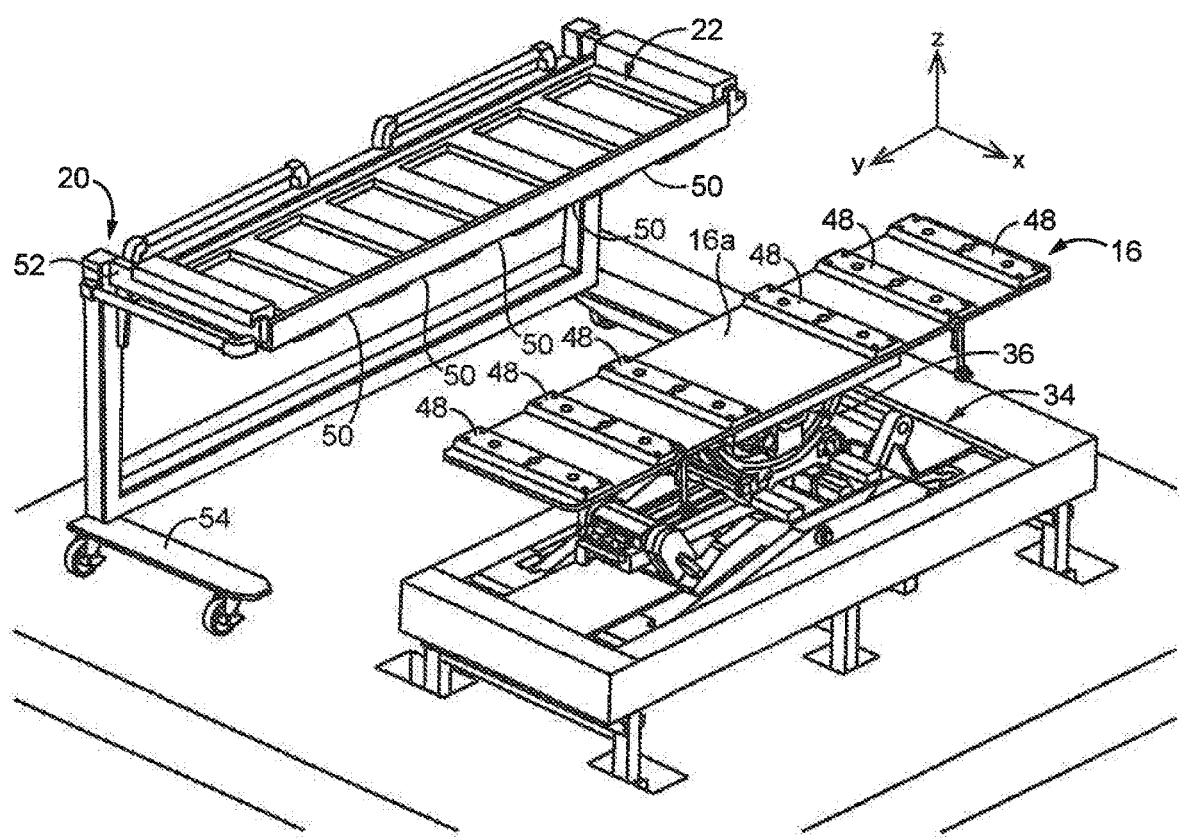
FIG. 4 is a detailed perspective view of a configuration of the irradiation table, a conveyance device, and a patient restraint/placement portion provided in the therapy system shown in FIG. 1.

In the present embodiment, the explanation is given of the therapy system 10 that is provided with the X-ray CT device as the three-dimensional diagnostic device 18. As shown in FIG. 2, the therapy system 10 is provided with the patient restraint/placement portion 22. In the treatment of the patient 8 using the therapy system 10, the patient 8 is placed and restrained on the patient restraint/placement portion 22. As shown in FIG. 4, he patient restraint/placement portion 22 is a flat plate-shaped member (table top) having a rectangular shape (a long rectangular shape) in a plan view, and edge portions that protrude upward toward the side of a top surface 22a, on which the patient 8 is placed, are provided around a peripheral edge portion of the rectangular-shaped member. Specifically, in other words, the patient restraint/placement portion 22 is a box-shaped member that does not have a top surface and that is rectangular in a plan view. In the treatment of the patient 8 using the therapy system 10, preferably, the patient 8 is placed on the patient restraint/placement portion 22 in a state of facing upward, and is restrained on the patient restraint/placement portion 22 using specific restraints that are not illustrated. The detection of the position of the affected part by the three-dimensional diagnostic device 18 shown in FIG. 2, the movement of the patient 8 between the three-dimensional diagnostic device 18 and the neutron beam irradiation device 14, and the irradiation of the neutron beams onto the affected part of the patient 8 by the neutron beam irradiation device, and the like are performed on the patient 8 who is placed and restrained on the patient restraint/placement portion 22 in the above-described manner.

A top portion of the irradiation table 16 shown in FIG. 1, and FIG. 3 to FIG. 8 is provided with a top surface plate 16a. The top surface plate 16a is a flat plate-shaped member that is a rectangular shape (a long rectangular shape) in a plan view, and preferably, is formed in substantially the same shape as the patient restraint/placement portion 22 in a plan view. A plurality of protruding portions 48 are provided on the surface of the top surface plate 16a. The patient restraint/placement portion 22 is placed and restrained on the top surface plate 16a. The top surface plate 16a is configured by a single material or a compound material that is not easily radioactivated, or if radioactivated, can suppress that radioactivity to a sufficiently small value. For example, the top surface plate 16a is formed by a resin block (polycarbonate) that is used to cause a metal plate and the patient restraint/placement portion 22 to be fitted together. Further, the top surface plate 16a may be configured from a material such as a carbon fiber reinforced plastic (carbon fibers that are cured using a synthetic resin, for example). By configuring the top surface plate 16a using such a material, when the top surface plate 16a is radioactivated by the neutron beams irradiated from the neutron beam irradiation device 14, a maximum exposure (dose equivalent) per hour of an employee is preferably 20 mSv or less. In the present embodiment, the employee corresponds to a person engaged in operations inside the room 12 when the patient 8 is irradiated with the neutron beams by the neutron beam irradiation device 14, and is, for example, a radiological technologist, a doctor, or a nurse. When the patient 8 is irradiated by the neutron beams from the neutron beam irradiation device 14, the employee transfers the patient restraint/placement portion 22 on which the patient 8 is placed from the conveyance device 20 to the irradiation table 16, for example. Further, the employee performs various operations relating to the irradiation of the neutron beams in the vicinity of the irradiation table 16. After performing the irradiation of the neutron beams, the employee is engaged in operations to move the patient restraint/placement portion 22 on which the patient 8 is placed from the irradiation table 16 to the conveyance device 20 and the like. When assuming the employee as described above, for example, the patient restraint/placement portion 22 that is fixed to the top surface plate 16a of the irradiation table 16 is positioned within a point-blank range of an irradiation port 14o of the neutron beam irradiation device 14, and a material is chosen such that, when the irradiation from the irradiation port 14o is performed for one hour, the radioactivation of the surface of the top surface plate 16a of the irradiation table 16 falls within a range that converts to a 20 mSv or less of exposure per hour of the employee at a maximum.

FIG. 2 is a diagram schematically illustrating a state in which the position of the affected part of the patient 8 is being detected by the three-dimensional diagnostic device 18. As shown in FIG. 2, the three-dimensional diagnostic device 18 is provided with a base 24, a self-propelling image capture unit 26 that captures three-dimensional images while moving in one direction (a y axis direction in the example shown in FIG. 2) with respect to the base 24, and a bed 28 on which the patient 8 (the patient restraint/placement portion 22 on which the patient 8 is restrained) is placed when performing the three-dimensional image capture. The bed 28 is preferably a rectangular shape in a plan view, and is provided such that a long direction of the bed 28 is the y axis direction shown in FIG. 2. The three-dimensional diagnostic device 18 is provided with a slide mechanism 30 that causes the bed 28 to move slidingly with respect to the base 24 in the y axis direction shown in FIG. 2, and a raising/lowering mechanism 32 that raises and lowers the bed 28 with respect to the base 24 in a z axis direction shown in FIG. 2.

When the three-dimensional image capture is performed by the three-dimensional diagnostic device 18, the patient 8 lies face up such that a head-to-toe direction is aligned with the movement direction of the self-propelling image capture unit 26 (namely, the y axis direction shown in FIG. 2). Specifically, the patient restraint/placement portion 22 on which the patient 8 is placed and restrained is placed on the bed 28 such that the head-to-toe direction of the patient 8 who is placed and restrained on the patient restraint/placement portion 22 in a state of facing upward is aligned with the movement direction of the self-propelling image capture unit 26 with respect to the base 24, and the three-dimensional image capture is performed by the self-propelling image capture unit 26.

Figure 3:
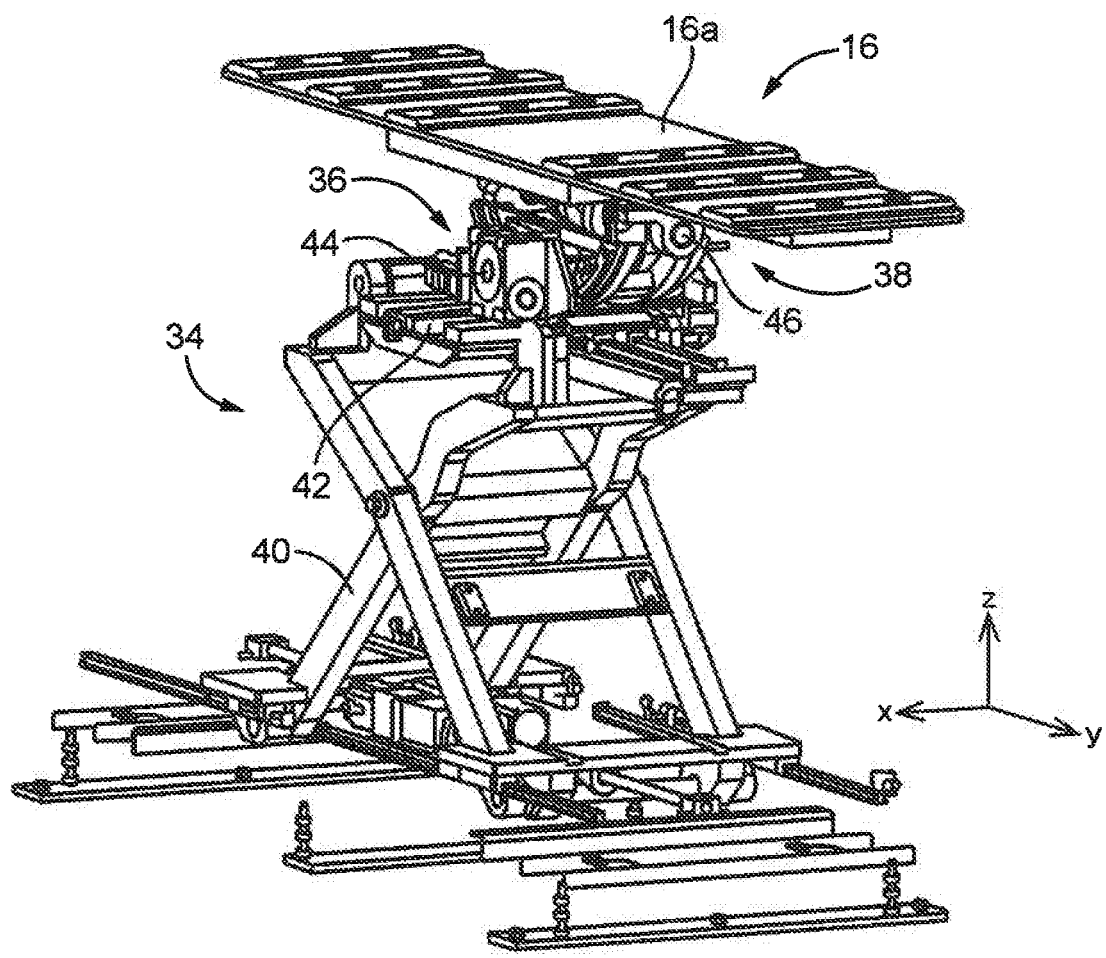
FIG. 3 is a detailed perspective view of a configuration of an irradiation table provided in the therapy system shown in FIG. 1.

FIG. 3 is a perspective view illustrating a configuration of the irradiation table 16. The irradiation table 16 is placed in the vicinity of the neutron beam irradiation device 14 in the room 12. A position of the patient restraint/placement portion 22 that is fixed to the top surface plate 16a is determined with respect to the neutron beam irradiation port 14o of the neutron beam irradiation device 14.

Figure 14:
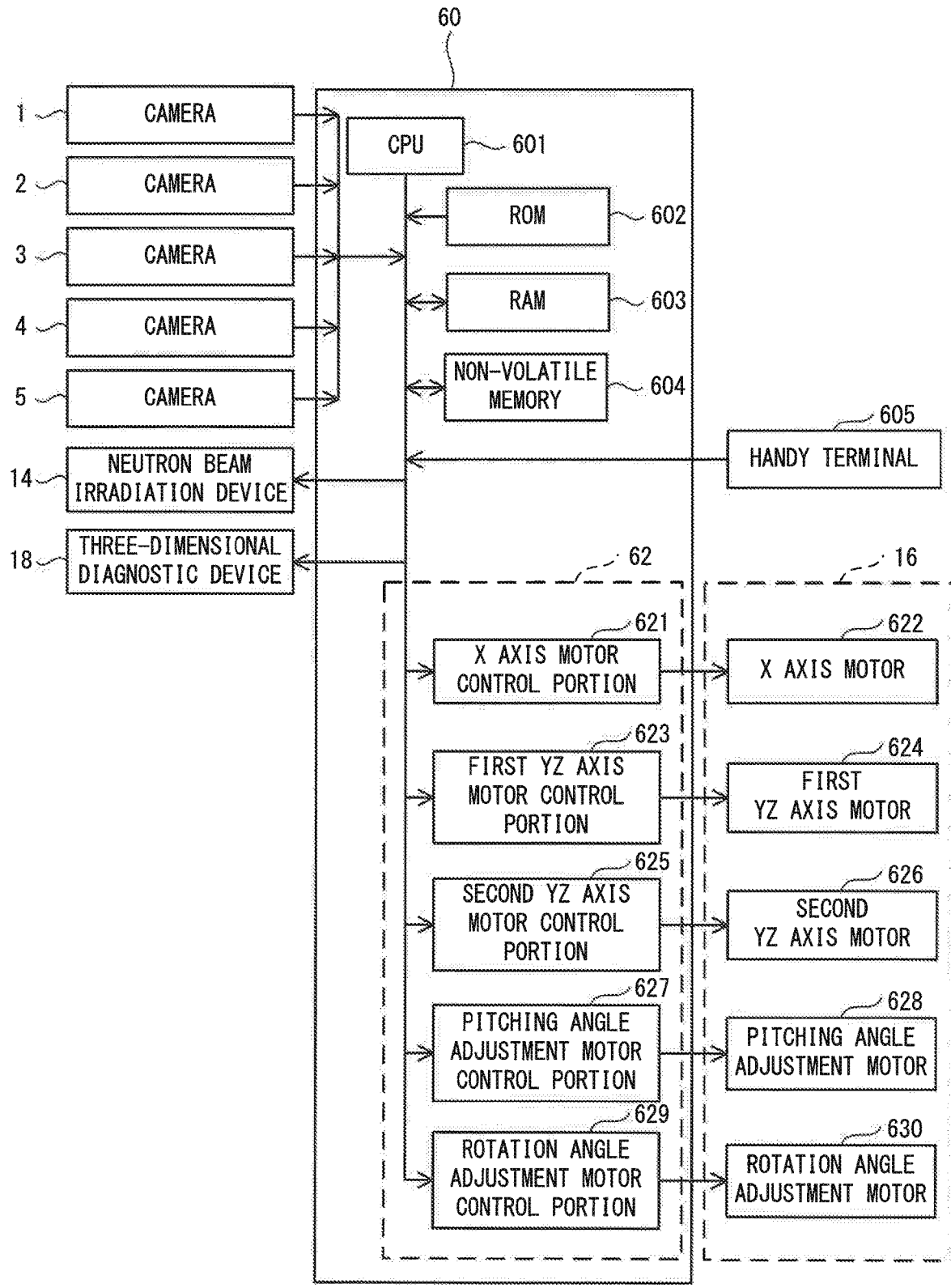
FIG. 14 is a block diagram showing an electrical configuration of a control unit 60.

The irradiation table 16 functions as a mechanism to determine the position of the patient restraint/placement portion 22 fixed to the top surface plate 16a with respect to the neutron beam irradiation port 14o of the neutron beam irradiation device 14, and is provided with a position adjustment mechanism 34, a first angle adjustment mechanism 36, and a second angle adjustment mechanism 38. The position adjustment mechanism 34 changes the position of the irradiation table 16 with respect to the irradiation port 14o of the neutron beam irradiation device 14, in relation to each of directions of three mutually orthogonal axes (translational axes). In FIG. 3, the three axes are indicated by the x, y, and z axes that are mutually orthogonal. The z axis direction corresponds to the vertical direction. The position adjustment mechanism 34 is provided with, for example, a y z axis movement arm 40 that causes the position of the irradiation table 16 with respect to the irradiation port 14o of the neutron beam irradiation device 14 to move in the y axis direction and the z axis direction shown in FIG. 3, and an x axis movement movable axis 42 that causes the position of the irradiation table 16 with respect to the neutron beam irradiation port 14o to move in the x axis direction shown in FIG. 3. The x axis movement movable axis 42 is driven by an X axis motor 622 shown in FIG. 14. Further, the y z axis movement arm 40 is driven by a first YZ axis motor 624 and a second YZ axis motor 626 shown in FIG. 14.

The first angle adjustment mechanism 36 changes an angle of the top surface plate 16a of the irradiation table 16 with respect to an irradiation direction of the neutron beams, centering on an axis that is parallel to one axis of the three axes. For example, a pitching angle adjustment axis 44 is provided that changes the angle of the top surface plate 16a with respect to the irradiation direction of the neutron beams from the neutron beam irradiation port 14o, around an axis that is parallel to the x axis direction shown in FIG. 3. The axis that is a center of the rotation by the first angle adjustment mechanism 36, for example, is an axis that is positioned in the center in the lengthwise direction of the top surface plate 16a in a plan view (when seen in the z axis direction) in parallel to the x axis, and is positioned at a predetermined height above the irradiation table 16 in the z axis direction. In the present embodiment, the angle adjusted by the first angle adjustment mechanism 36 is referred to as a pitching angle. In other words, the top surface plate 16a is configured such that the pitching angle thereof with respect to the irradiation direction of the neutron beams is changed by the top surface plate 16a being rotated around the axis by the first angle adjustment mechanism 36. The pitching angle adjustment axis 44 is driven by a pitching angle adjustment motor 628 shown in FIG. 14.

The second angle adjustment mechanism 38 changes an angle of the top surface plate 16a with respect to the irradiation direction of the neutron beams from the neutron beam irradiation port 14o, centering on an axis that is parallel to one axis that is different to the above axis, among the three axes. For example, the angle of the top surface plate 16a with respect to the irradiation direction of the neutron beams from the neutron beam irradiation port 14o is changed around a rotation angle adjustment axis 46 that is parallel to the y axis direction shown in FIG. 3. In the present embodiment, an angle centering on the rotation angle adjustment axis 46 is referred to as a rotation angle. In other words, the top surface plate 16a is configured such that the rotation angle thereof with respect to the irradiation direction of the neutron beams is changed by the top surface plate 16a being rotated around the rotation angle adjustment axis 46. The rotation angle adjustment axis 46 is driven by a rotation angle adjustment motor 630 shown in FIG. 14.

As described above, the irradiation table 16 is provided with the position adjustment mechanism 34, the first angle adjustment mechanism 36, and the second angle adjustment mechanism 38. Thus, the positions in the x, y, and z axis direction of the top surface plate 16a with respect to the irradiation port 14o of the neutron beam irradiation device 14 can all respectively be changed, and at the same time, the pitching angle of the top surface plate 16a around the axis parallel to the x axis, and the rotation angle of the top surface plate 16a around the axis parallel to the y axis can be changed. Preferably, as shown in FIG. 3, between a floor plate and the top surface plate 16a, the y z axis movement arm 40, the x axis movement movable axis 42, the pitching adjustment axis 44, and the rotation angle adjustment axis 46 are provided, in that order, from the floor surface side toward the top surface plate 16a side. The y z axis movement arm 40 and the like are driven, for example, by power generated by an electric motor and the like to be described later, in accordance with commands supplied from a control unit 60 to be described later, thus realizing the movement of the top surface plate 16a. The top surface plate 16a of the irradiation table 16 is mechanically coupled to the rotation angle adjustment axis 46.

FIG. 4 to FIG. 8 are perspective views showing configurations of the irradiation table 16, the conveyance mechanism 20, and the patient restraint/placement portion 22. As shown in FIG. 4 and so on, the patient restraint/placement portion 22 and the top surface plate 16a are provided with engagement structures that are caused to engage with each other in sections that face each other when the patient restraint/placement portion 22 is placed on the top surface plate 16a. Specifically, the plurality of protruding portions 48, which protrude to the top surface side from the top surface plate 16a, are provided on the surface of the top surface plate 16a. The protruding portions 48 are protruding portions that extend in a short axis direction of the top surface plate 16a (the x axis direction shown in FIG. 4). A plurality of groove portions 50 are provided in the bottom surface of the patient restraint/placement portion 22, in positions in which they can be engaged with the plurality of protruding portions 48. The groove portions 50 are groove portions that extend in the short axis direction of the patient restraint/placement portion 22 (the x axis direction shown in FIG. 4). When the patient restraint/placement portion 22 is placed on the irradiation table 16, the protruding portions 48 formed on the irradiation table 16 engage with the groove portions 50 formed in the patient restraint/placement portion 22, and the position of the patient restraint/placement portion 22 with respect to the irradiation table 16 is determined. Both the protruding portions 48 and the groove portions 50 are formed in a longitudinal shape in the short axis direction of the patient restraint/placement portion 22 and the irradiation table 16, and thus, at least the movement of the patient restraint/placement portion 22 with respect to the top surface plate 16a of the irradiation table 16 in the long axis direction (the y axis direction shown in FIG. 4) is restricted. As will be described later with reference to FIG. 8, the patient restraint/placement portion 22 is configured so as to be able to be offset with respect to the irradiation table 16 in relation to the y axis direction shown in FIG. 4, by displacing the engagement positions of the protruding portions 48 and the groove portions 50.

Figure 5:
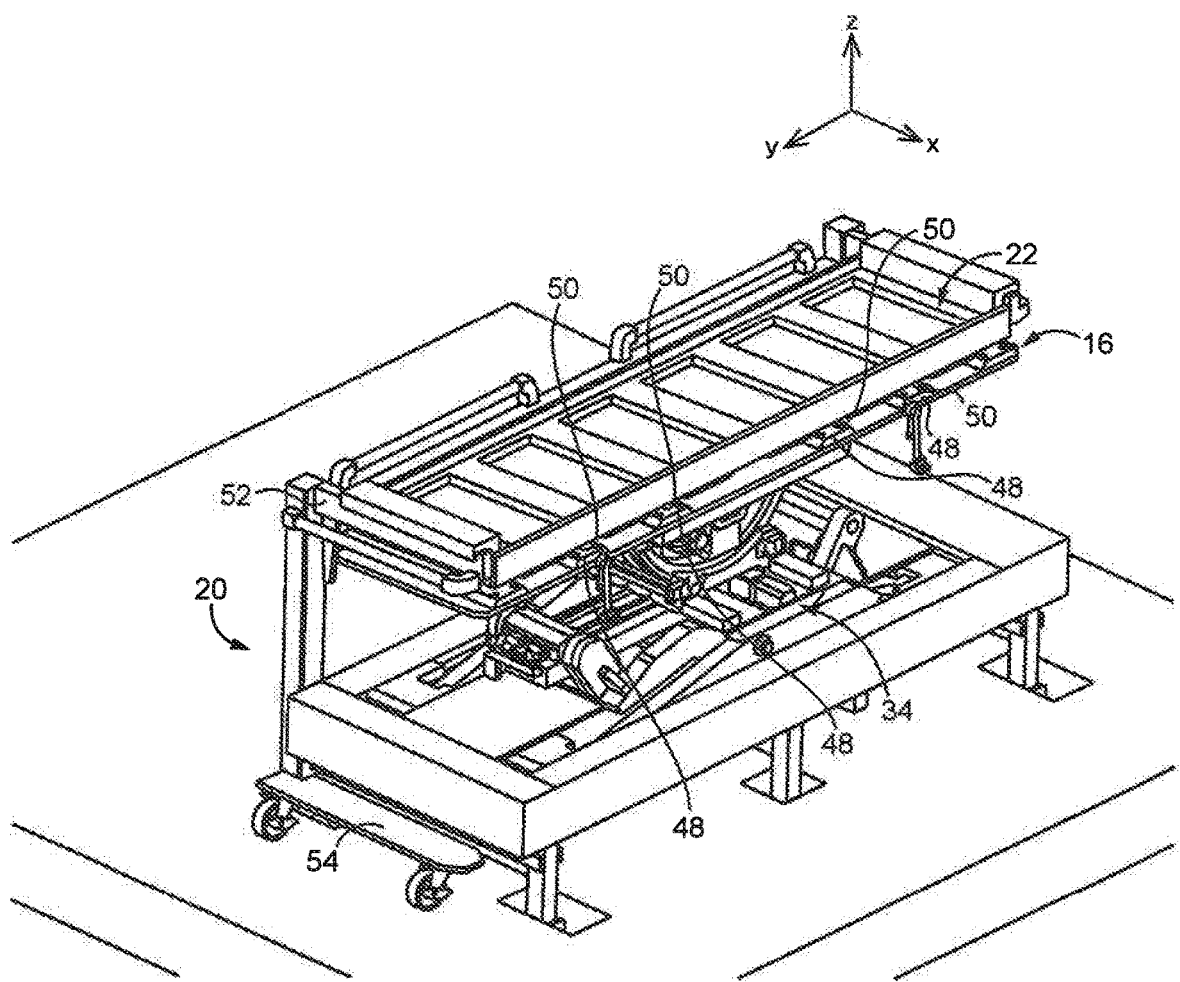
FIG. 5 is a detailed perspective view of the configuration of the irradiation table, the conveyance device, and the patient restraint/placement portion provided in the therapy system shown in FIG. 1.

FIG. 4 shows a state in which the patient restraint/placement portion 22 is placed on the conveyance mechanism 20. In the present embodiment, the conveyance mechanism 20 conveys the patient restraint/placement portion 22, on which the patient 8 is placed and restrained, between the three-dimensional diagnostic device 18 and the irradiation table 16. Further, the conveyance mechanism 20 functions as a transfer device to transfer the patient restraint/placement portion 22 onto the top surface plate 16a. As shown in FIG. 4 and FIG. 5, the conveyance mechanism 20 is provided with a holding portion 52 and a caster portion 54. The holding portion 52 holds the patient restraint/placement portion 22 in its placed state, and is fork-shaped such that, after the patient restraint/placement portion 22 has been transferred to the three-dimensional diagnostic device 18 or the irradiation table 16, the holding portion 52 can be pulled out. The caster portion 54 is provided with a plurality of wheels and moves the conveyance mechanism 20 as a result of the rolling of the wheels on the floor surface. The conveyance mechanism 20 may be provided with a raising/lowering mechanism that raises and lowers the patient restraint/placement portion 22 placed on the holding portion 52. Using the raising/lowering mechanism provided on the conveyance mechanism 20, the raising/lowering mechanism 32 provided on the three-dimensional diagnostic device 18 shown in FIG. 2, or the position adjustment mechanism 34, the conveyance mechanism 20 transfers the patient restraint/placement portion 22 on which the patient 8 is restrained between the conveyance mechanism 20 and the three-dimensional diagnostic device 18 or the top surface plate 16a of the irradiation table 16.

Figure 6:
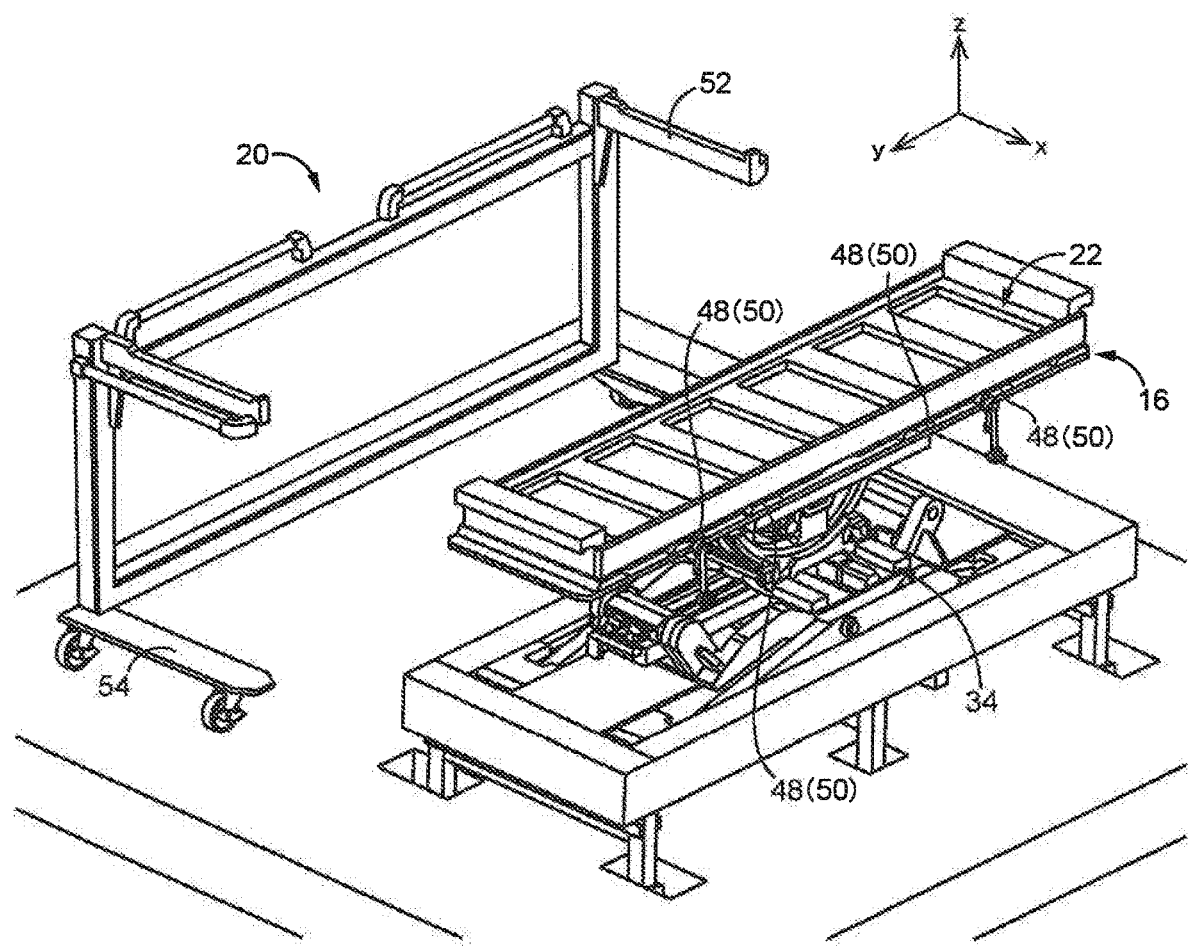
FIG. 6 is a detailed perspective view of the configuration of the irradiation table, the conveyance device, and the patient restraint/placement portion provided in the therapy system shown in FIG. 1.

Below, with reference to FIG. 4 to FIG. 6, the transfer of the patient restraint/placement portion 22 from the conveyance mechanism 20 to the top surface plate 16a of the irradiation table 16 will be described. In FIG. 4 to FIG. 8, for convenience, the patient restraint/placement portion 22 on which the patient 8 is not placed is illustrated. In actual treatment using the therapy system 10, the transfer described below is performed while the patient 8 is placed and restrained on the patient restraint/placement portion 22. FIG. 4 shows a state in which the patient restraint/placement portion 22 is placed on the conveyance mechanism 20. In this state, the conveyance mechanism 20 is moved over the floor surface by the caster portion 54, and the patient restraint/placement portion 22 held by the holding portion 52 is conveyed.

FIG. 5 illustrates a state in which, due to the conveyance of the conveyance mechanism 20, the patient restraint/placement portion 22 has been moved vertically above the top surface plate 16a of the irradiation table 16. In other words, FIG. 5 illustrates a state in which the top surface plate 16a of the irradiation table 16 is positioned vertically below the patient restraint/placement portion 22 held by the holding portion 52. Here, as shown in FIG. 5, the position of the patient restraint/placement portion 22 with respect to the top surface plate 16a of the irradiation table 16 is adjusted in the x axis direction and the y axis direction such that the protruding portions 48 formed on the top surface plate 16a of the irradiation table 16 and the groove portions 50 formed in the bottom surface of the patient restraint/placement portion 22 are in mutually corresponding positions. From this state, if the top surface plate 16a of the irradiation table 16 is raised in the z axis direction using the position adjustment mechanism 34, the top surface plate 16a lifts up the patient restraint/placement portion 22, and the patient restraint/placement portion 22 is separated from the holding portion 52 of the conveyance mechanism 20.

FIG. 6 illustrates a state in which the transfer of the patient restraint/placement portion 22 from the conveyance mechanism 20 to the irradiation table 16 is complete. From the state in which the top surface plate 16a of the irradiation table 16 has lifted the patient restraint/placement portion 22 and the patient restraint/placement portion 22 is separated from the holding portion 52 of the conveyance mechanism 20, when the conveyance mechanism 20 is moved (retracted) in the x axis direction shown in FIG. 6, the holding portion 52 is pulled out from below the patient restraint/placement portion 22. At this time, since the protruding portions 48 formed on the top surface plate 16a of the irradiation table 16, and the groove portions 50 formed in the bottom surface of the patient restraint/placement portion 22 are in the mutually corresponding positions, as shown in FIG. 6, the protruding portions 48 and the groove portions 50 are caused to engage with each other.

Figure 7:
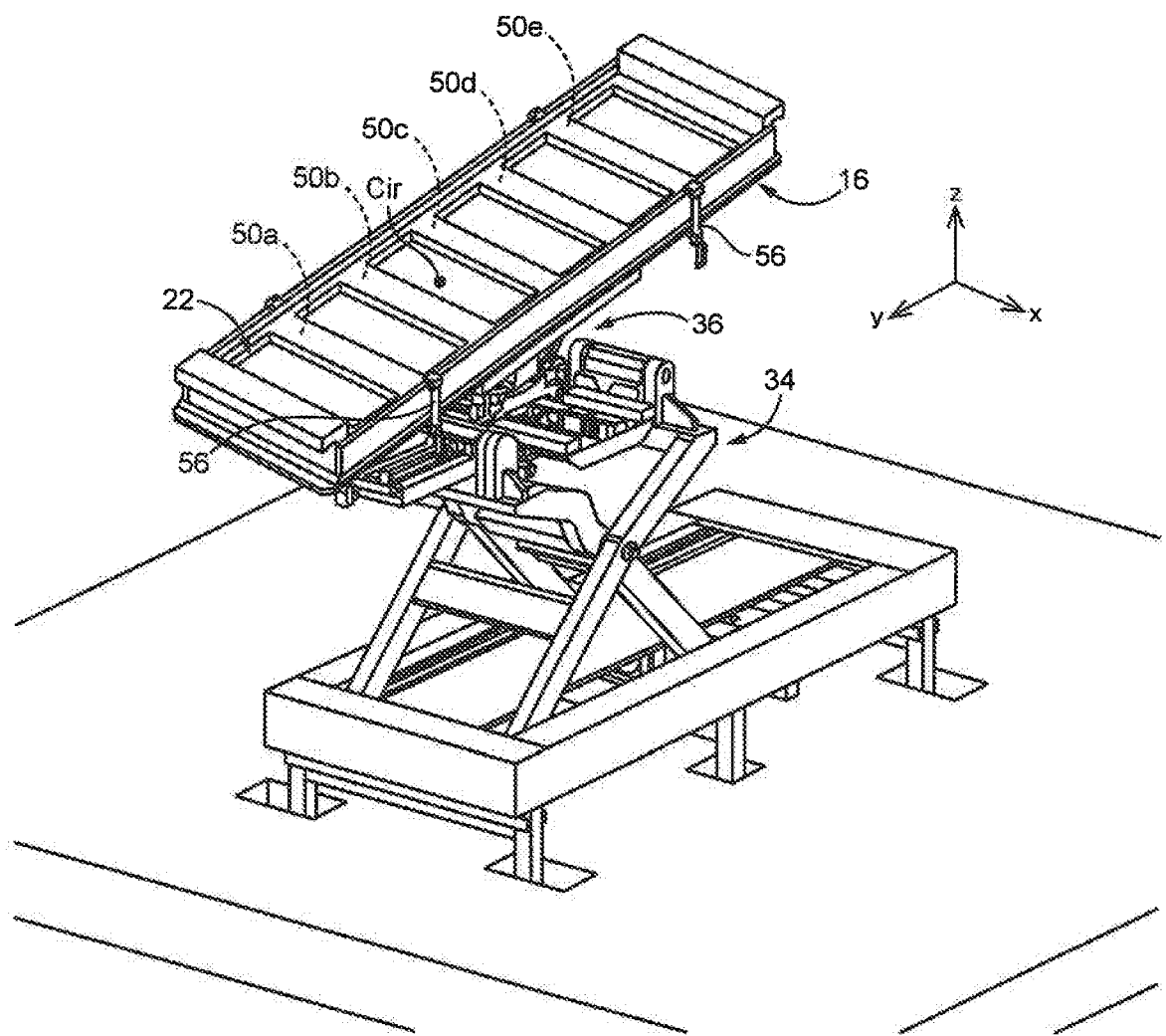
FIG. 7 is a perspective view illustrating a state in which a position of the irradiation table provided in the therapy system shown in FIG. 1 is being changed.
Figure 8:
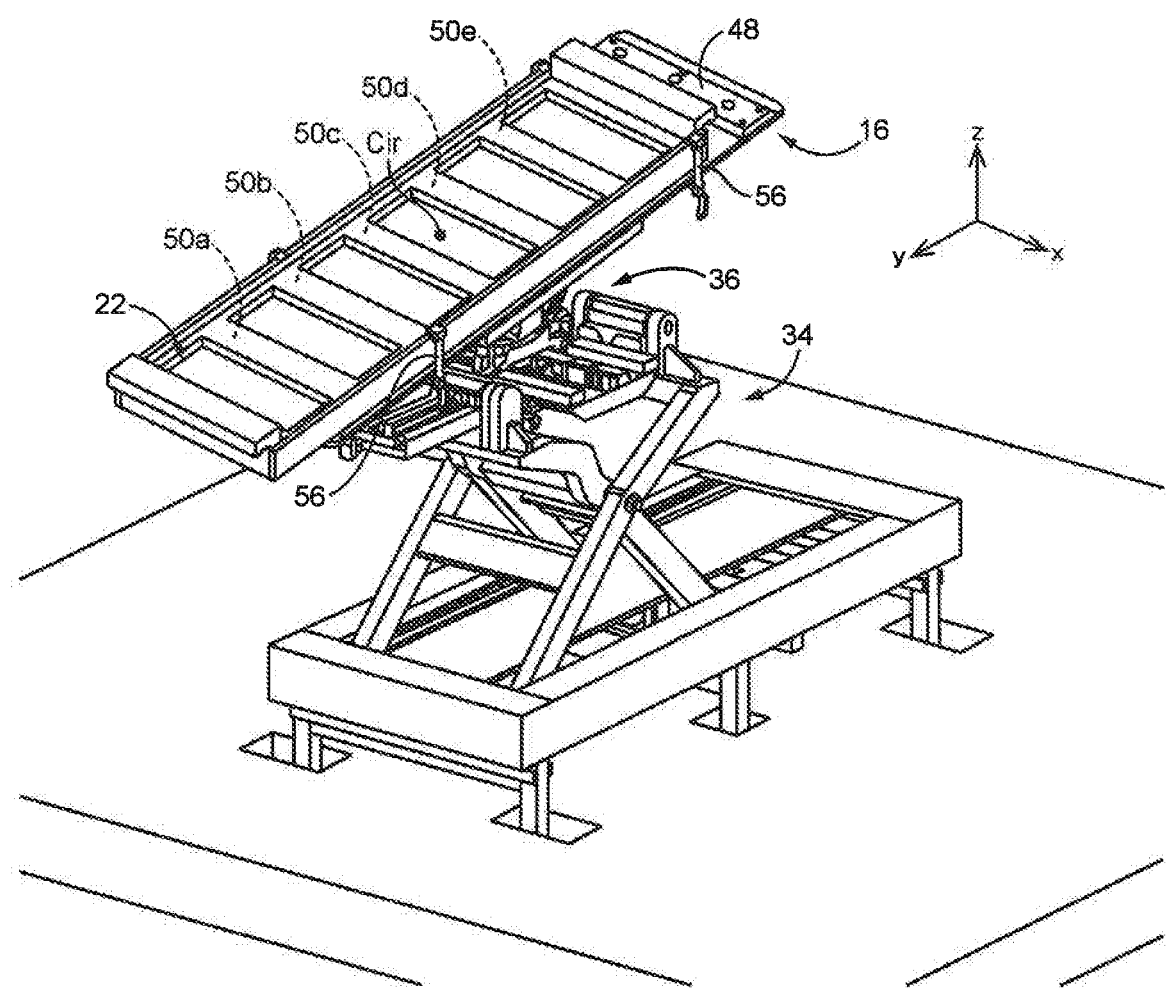
FIG. 8 is a diagram showing a state in which an engagement position of the patient restraint/placement portion and the irradiation table has been displaced from the state shown in FIG. 7, and has been offset in a y direction.

FIG. 7 is a perspective view showing a state in which a position of the top surface plate 16a on which the patient restraint/placement portion 22 is placed is changed using the position adjustment mechanism 34, the first angle adjustment mechanism 36, and the second angle adjustment mechanism 38. FIG. 8 shows a state, from the state shown in FIG. 7, in which the engagement positions of the protruding portions 48 and the groove portions 50 are displaced, and the patient restraint/placement portion 22 is offset in the y axis direction with respect to the top surface plate 16a. In FIG. 7 and FIG. 8, in order to distinguish between the plurality of groove portions 50, they are indicated as groove portions 50a, 50b, 50c, 50d, and 50e. As shown in FIG. 7 and FIG. 8, the patient restraint/placement portion 22 placed on the top surface plate 16a is fixed to the top surface plate 16a by a fastening portion 56. The state shown in FIG. 7 illustrates a state in which the patient restraint/placement portion 22 has not been offset with respect to the top surface plate 16a in the y axis direction (y axis offset=0 mm). When an interval in the y axis direction between the plurality of groove portions 50 (namely, an interval between the plurality of protruding portions 48) is 300 mm, when the engagement positions between the protruding portions 48 and the groove portions 50 are displaced by one (in FIG. 7, the protruding portion 48 that was engaged with the groove portion 50c is engaged with the groove portion 50d, for example), the patient restraint/placement portion 22 is offset (the position is changed in the y axis direction) by 300 mm with respect to the top surface plate 16a.

In FIG. 7 and FIG. 8, a center position of the neutron beam irradiation port 14o (refer to FIG. 10) of the neutron beam irradiation device 14 is denoted by Cir. When the patient restraint/placement portion 22 is offset with respect to the top surface plate 16a, the center position of the neutron beam irradiation port 14o in the patient restraint/placement portion 22 moves in the y axis direction. For example, in the state shown in FIG. 7, the center position Cir of the neutron beam irradiation port 14o faces a position between the groove portions 50b and 50c. In the state in which, from this state, the engagement positions of the protruding portions 48 and the groove portions 50 has been displaced by one (refer to FIG. 8), the center position Cir of the neutron beam irradiation port 14o faces a position between the groove portions 50c and 50d. More specifically, when the patient restraint/placement portion 22 is offset by 300 mm with respect to the top surface plate 16a, the center position Cir of the neutron beam irradiation port 14o with respect to the patient restraint/placement portion 22 moves by 300 mm in the opposite direction, in the y axis direction. In other words, the center position Cir of the neutron beam irradiation port 14o with respect to the patient 8 placed and restrained on the patient restraint/placement portion 22 moves in the y axis direction. In this way, by displacing the engagement positions between the protruding portions 48 and the groove portions 50, the center position Cir of the neutron beam irradiation port 14o with respect to the patient 8 can be adjusted while the patient 8 remains restrained in the state of being placed on the patient restraint/placement portion 22.

As shown in FIG. 1, the therapy system 10 is provided with the control unit 60. Next, an example of an electrical configuration of the control unit 60 will be described with reference to FIG. 14. The control unit 60 is provided with a CPU 601, a ROM 602, a RAM 603, a non-volatile memory 604, and a position adjustment portion 62. The CPU 601 executes various controls relating to the therapy system 10 by performing signal processing in accordance with a program stored in advance in the ROM 602, while using temporary storage functions of the RAM 603. As a result, the CPU 601 of the control unit 60 controls the position adjustment mechanism 34, the first angle adjustment mechanism 36, and the second angle adjustment mechanism 38 of the irradiation table 16. Further, the CPU 601 receives, from the three-dimensional diagnostic device 18 and treatment planning software, information about the position and an attitude angle of the tumor. In control terms, the CPU 601 is not combined with the neutron beam irradiation device 14. However, using commands of a surgeon, the CPU 601 of the control unit 60, and a CPU (not illustrated) of a control portion of the neutron beam irradiation device 14 have mutually coordinated timings. The ROM 602 stores an operating system, various programs, and various data. The RAM 603 temporarily stores various data. The non-volatile memory 604 stores and holds various data.

An X axis motor control portion 621, a first YZ axis motor control portion 623, a second YX axis motor control portion 625, a pitching angle adjustment motor control portion 627, and a rotation angle adjustment motor control portion 629 are provided in the position adjustment portion 62. The X axis motor control portion 621 controls the X axis motor 622. The first YZ axis motor control portion 623 controls the first YZ axis motor 624. The second YZ axis motor control portion 625 controls the second YZ axis motor 626. The pitching angle adjustment motor control portion 627 controls the pitching angle adjustment motor 628. The rotation angle adjustment motor control portion 629 controls the rotation angle adjustment motor 630. The CPU 601 controls each of the control portions of the position adjustment portion 62. Thus, each of the motors are controlled by commands from the CPU 601, and the movement of the position in the x, y, and z axis directions, and the changes in the pitching angle and the rotation angle of the top surface plate 16*a* are controlled so as to be movable in five axis directions. Further, an output of the cameras 1 to 5 is input to the CPU 601. In addition, a handy terminal 605 is connected to the control unit 60, and an output of the handy terminal 605 is input to the CPU 601. The handy terminal 605 is provided with keys, a display portion and the like that are not illustrated, and can be used to input commands to control the position adjustment portion 62.

Further, the handy terminal 605 can be mounted on and removed from the control unit 60, and a configuration is adopted in which, at the time of the irradiation of the neutron beams by the neutron beam irradiation device 14, the handy terminal 605 is removed and carried out from the room 12. In addition, the CPU 601 of the control unit 60 controls operations of the neutron beam irradiation device 14 and operations of the three-dimensional diagnostic device 18. The CPU 601 executes control to change the position of the top surface plate 16*a* with respect to the neutron beam irradiation port 14*o* of the neutron beam irradiation device 14, using at least one of the position adjustment mechanism 34, the first angle adjustment mechanism 36, and the second angle adjustment mechanism 38. Specifically, using the position adjustment mechanism 34, the CPU 601 performs control to change the position, in each of the directions of the three axes (the x, y, and z axes shown in FIG. 3 and the like), of the top surface plate 16*a* onto which the patient restraint/placement portion 22 has been transferred. Further, using the pitching angle adjustment axis 44, the CPU 601 performs control to change the pitching angle of the top surface plate 16*a* onto which the patient restraint/placement portion 22 has been transferred. In addition, using the rotation angle adjustment axis 46, the CPU 601 performs control to change the rotation angle of the top surface plate 16*a* onto which the patient restraint/placement portion 22 has been transferred. By the above-described controls, the CPU 601 aligns the position of the affected part of the patient 8 detected by the three-dimensional diagnostic device 18 and the position of the neutron beams irradiated by the neutron beam irradiation device 14, and performs control to cause the affected part to come as close as possible to the neutron beam irradiation port 14*o*.

As shown in FIG. 1, the three-dimensional diagnostic device 18 is provided with a pair of horizontal direction lasers 64*a* and 64*b*, and a vertical direction laser 66, which perform display to verify positions corresponding to a coordinate system relating to the three-dimensional image capture by the three-dimensional diagnostic device 18. The horizontal direction lasers 64*a* and 64*b*, and the vertical direction laser 66 need not necessarily be integrally provided in the three-dimensional diagnostic device 18, and may be provided separately from the three-dimensional diagnostic device 18 inside the room in which the three-dimensional diagnostic device 18 is installed. The neutron beam irradiation device 14 is provided with a pair of horizontal direction lasers 68*a* and 68*b*, and a vertical direction laser 70, which perform display to verify positions of the neutron beams irradiated from the neutron beam irradiation port 14*o* of the neutron beam irradiation device 14. The horizontal direction lasers 68*a* and 68*b*, and the vertical direction laser 70 need not necessarily be integrally provided in the neutron beam irradiation device 14, and may be provided separately from the neutron beam irradiation device 14 in the room 12 in which the neutron beam irradiation device 14 is installed. In the present embodiment, the horizontal direction lasers 64*a* and 64*b*, and the vertical direction laser 66 provided in the three-dimensional diagnostic device 18, and the horizontal direction lasers 68*a* and 68*b*, and the vertical direction laser 70 provided in the neutron beam irradiation device 14 correspond to a position display portion that performs display to verify that the position of the affected part of the patient 8 detected by the three-dimensional diagnostic device 18 is sufficiently aligned with the position of the neutron beams irradiated from the neutron beam irradiation device 14.

The horizontal direction lasers 64*a* and 64*b*, and the vertical direction laser 66 provided in the three-dimensional diagnostic device 18 are preferably movable devices whose position can be changed with respect to the bed 28 (the patient 8), and the position thereof is controlled by a control device, such as the control unit 60. Preferably, as shown in FIG. 9 to be described later, as well as the positions in the vertical direction (the positions in the z axis direction) of the horizontal direction lasers 64*a* and 64*b* being changed, the position in the horizontal direction (the position in the x axis direction) of the vertical direction laser 66 is changed.

Figure 9:
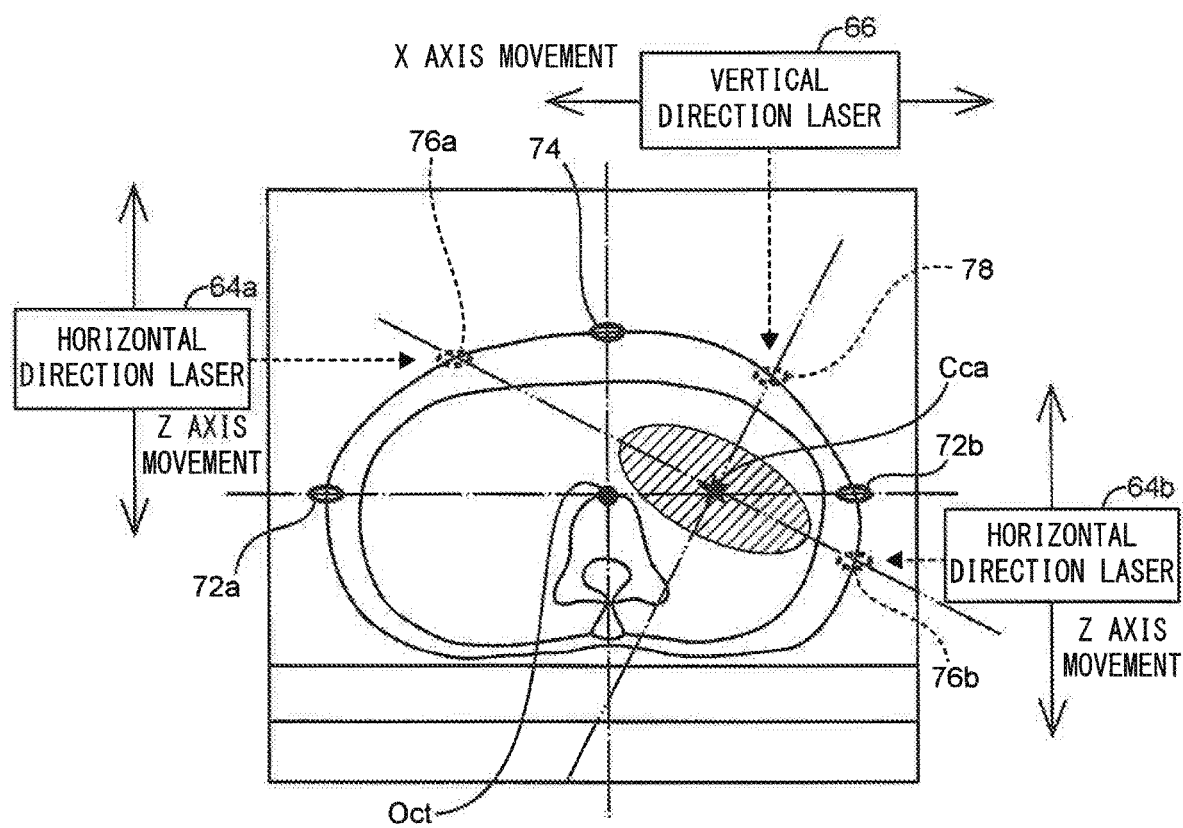
FIG. 9 is a diagram illustrating an image corresponding to one cross-section in a three-dimensional image captured by the three-dimensional diagnostic device shown in FIG. 2.

FIG. 9 is a diagram illustrating an image corresponding to one cross-section in the three-dimensional image captured by the three-dimensional diagnostic device 18. In FIG. 9, display positions by the position display portion are also illustrated on the captured image of the body of the patient 8. When the three-dimensional image of the patient 8 is captured by the three-dimensional diagnostic device 18, the pair of horizontal direction lasers 64*a* and 64*b* and the vertical direction laser 66 irradiate laser light onto the body of the patient 8, and thus cause a position corresponding to the coordinate system relating to the capture of the three-dimensional image to be displayed. In FIG. 9, a display by the horizontal direction laser 64*a* is shown by a position 72*a*, a display by the horizontal direction laser 64*b* is shown by a position 72*b*, and a display by the vertical direction laser 66 is shown by a position 74, respectively. When the three-dimensional image is captured by the three-dimensional diagnostic device 18, the positions 72*a*, 72*b*, and 74 displayed on the body of the patient 8 by the pair of horizontal direction lasers 64*a* and 64*b* and the vertical direction laser 66 correspond to an origin point Oct (a CT origin point, for example) relating to the image capture of the three-dimensional diagnostic device 18. In FIG. 9, the coordinate system relating to the detection is shown using lines of alternate long and short dashes. For example, an intersection point between a straight line joining the display positions 72a and 72b by the pair of horizontal direction lasers 64a and 64b, and a straight line that is a straight line perpendicular to the above straight line and that passes through the display position 74 by the vertical direction laser 66 corresponds to the origin point Oct relating to the image capture by the three-dimensional diagnostic device 18.

In the three-dimensional image captured by the three-dimensional diagnostic device 18, when the affected part of the patient 8 is detected, an irradiation area can be set over which to perform the treatment on the affected part. Specifically, a treatment plan by the neutron beam irradiation device 14 can be devised in accordance with the detected affected part. In the treatment plan, the irradiation positions and the irradiation directions of the neutron beams irradiated from the neutron beam irradiation port 14o with respect to the patient 8 are determined. As described above, although the neutron beam irradiation device 14 is preferably a device that irradiates the neutron beams onto the patient 8 from vertically above, the neutron beam irradiation device 14 can change the irradiation position and the irradiation direction of the neutron beams irradiated from the neutron beam irradiation device 14 by changing the position, the angle and the like of the patient 8 with respect to the neutron beam irradiation port 14o of the neutron beam irradiation device 14.

In FIG. 9, as well as showing a tumor central position Cca using a star symbol in the three-dimensional image, with respect to the positions of the neutron beams to be used to effectively perform the treatment at the tumor central position Cca, a display by the horizontal direction laser 68a is shown by a position 76a, a display by the horizontal direction laser 68b is shown by a position 76b, and a display by the vertical direction laser 70 is shown by a position 78, respectively. At the time of the irradiation of the neutron beams onto the patient 8 by the neutron beam irradiation device 14, the pair of horizontal direction lasers 68a and 68b, and the vertical direction laser 70 cause the positions of the neutron beams irradiated from the neutron beam irradiation device 14 to be displayed by irradiating the laser light onto the body of the patient 8. Specifically, the positions 76a, 76b, and 78 displayed on the body of the patient 8 by the pair of horizontal direction lasers 68a and 68b, and the vertical direction laser 70 correspond to the irradiation positions and the irradiation directions with respect to the body of the patient 8, of the neutron beams irradiated from the neutron beam irradiation device 14. Thus, when the treatment plan by the neutron beam irradiation device 14 is devised and the irradiation positions and the irradiation directions of the neutron beams irradiated by the neutron beam irradiation device 14 are determined on the basis of the three-dimensional image captured by the three-dimensional diagnostic device 18, the positions 76a, 76b, and 78 to be displayed on the body of the patient 8 by the pair of horizontal direction lasers 68a and 68b, and the vertical direction laser 70 are established in accordance with the irradiation positions and the irradiation directions of the neutron beams. In FIG. 9, the coordinate system relating to the positions of the neutron beams is shown using lines of alternate long and two short dashes.

When the treatment plan by the neutron beam irradiation device 14 is devised and the irradiation positions and the irradiation directions of the neutron beams by the neutron beam irradiation device 14 are determined on the basis of the three-dimensional image captured by the three-dimensional diagnostic device 18, the control unit 60 controls the positions of the horizontal direction lasers 64a and 64b, and the vertical direction laser 66 such that the display positions 72a, 72b and 74 by the horizontal direction lasers 64a and 64b, and the vertical direction laser 66 with respect to the patient 8 are aligned with the display positions 76a, 76b, and 78 of the horizontal direction lasers 68a and 68b, and the vertical direction laser 70 with respect to the patient 8 at the time of the treatment using the neutron beam irradiation device 14. Specifically, as well as changing the position of each of the horizontal direction lasers 64a and 64b in the z axis direction, the position of the vertical direction laser 66 is changed in the x axis direction, and the irradiation of the laser light is performed. According to this mode, in a diagnosis using the three-dimensional diagnostic device 18, by affixing marks to the display positions of the horizontal direction lasers 64a and 64b, and the vertical direction laser 66 whose positions have been changed in accordance with the position of the detected affected part, at the time of the treatment using the neutron beam irradiation device 14, the positions that should be displayed by the horizontal direction lasers 68a and 68b, and the vertical direction laser 70 can be easily indicated.

As described above, the pair of horizontal direction lasers 64a and 64b, and the vertical direction laser 66 provided in the three-dimensional diagnostic device 18, and the pair of horizontal direction lasers 68a and 68b, and the vertical direction laser 70 provided in the neutron beam irradiation device 14 perform the display in order to verify that an imaging reference point of the three-dimensional image captured by the three-dimensional diagnostic device 18 is sufficiently aligned with respect to the coordinate system corresponding to the directions of the three axes of the irradiation table 16. In the treatment of the patient 8 using the therapy system 10, at the time of the image capture of the three-dimensional image relating to the patient 8 by the three-dimensional diagnostic device 18, preferably, the marks (markings) are affixed using markers or the like, to the positions 72a, 72b, and 74 displayed on the body of the patient 8 by the horizontal direction lasers 64a and 64b, and the vertical direction laser 66. These marks are preferably affixed by a human operation, but may be affixed without requiring human operation, by a method such as applying in advance a material that changes color in response to laser light on the body of the patient 8. As a material of the marks, a material is preferably used by which, on the three-dimensional image captured by the three-dimensional diagnostic device 18, there is a sufficient distinction between a main material of the patient restraint/placement portion 22 and the marks.

In the treatment of the patient 8 using the therapy system 10, marks are preferably affixed using markers or the like to the positions 76a, 76b, and 78 to be displayed on the patient 8 by the pair of horizontal direction lasers 68a and 68b, and the vertical direction laser 70 of the neutron beam irradiation device 14, in correspondence to the position of the affected part detected on the basis of the three-dimensional image captured by the three-dimensional diagnostic device 18, before the irradiation of the neutron beams by the neutron beam irradiation device 14. The material of the marks may be the same material as the marks relating to the diagnosis by the three-dimensional diagnostic device 18, but preferably, a material is used that allows at least sufficient visual distinction between this and the other material.

As shown in FIG. 1, the control unit 60 is provided with the position adjustment portion 62. The position adjustment portion 62 may be provided as a functional portion of the control unit 60, or may be provided as a separate control device to the control unit 60. By causing the position adjustment mechanism 34 to change the position in relation to each of the directions of the three axes of the top surface plate 16a onto which the patient restraint/placement portion 22 has been transferred, on the basis of the marks corresponding to positional coordinates relating to the detection that are affixed to the patient 8 when detecting the position of the affected part using the three-dimensional diagnostic device 18, the position adjustment portion 62 aligns the position of the affected part of the patient 8 detected by the three-dimensional diagnostic device 18 with the position of the neutron beams irradiated from the neutron beam irradiation device 14.

On the basis of the marks affixed to the positions 76a, 76b, and 78 to be displayed on the body of the patient 8 by the horizontal direction lasers 68a and 68b, and the vertical direction laser 70 of the neutron beam irradiation device 14, the position adjustment portion 62 performs position adjustment at the time of the actual treatment using the neutron beam irradiation device 14 such that the positions displayed on the body of the patient 8 by the horizontal direction lasers 68a and 68b, and the vertical direction laser 70 are aligned with the positions to which the marks are affixed. Specifically, at least one of the position adjustment mechanism 34, the first angle adjustment mechanism 36, and the second angle adjustment mechanism 38 is adjusted such that an error between the positions displayed on the body of the patient 8 by the horizontal direction lasers 68a and 68b, and the vertical direction laser 70, and the positions to which the marks are affixed is within a prescribed permissible range. Specifically, adjustment is performed such that an error of the imaging reference point of the three-dimensional image by the three-dimensional diagnostic device 18 corresponding to the coordinate system relating to the directions of the three axes of the irradiation table 16 is within a prescribed permissible range. Preferably, the adjustment by the position adjustment portion 62 is performed by the human operation while the surgeon visually verifies a displacement between the positions displayed on the body of the patient 8 by the horizontal direction lasers 68a and 68b, and the vertical direction laser 70 and the positions to which the marks have been affixed, but the adjustment may be automatically performed by capturing an image the body of the patient 8 and causing the positions of the marks in the captured image and the laser light irradiation positions to be aligned.

Below, an example will be described in detail of a specific treatment using the therapy system 10. In the treatment using the therapy system 10, first, the three-dimensional image of the inside of the body of the patient 8 is captured by the three-dimensional diagnostic device 18, and the treatment plan is devised on the basis of the three-dimensional image. In the diagnosis by the three-dimensional diagnostic device 18, first, the patient restraint/placement portion 22 is placed on the bed 28 of the three-dimensional diagnostic device 18. Next, along with the patient 8 being caused to lie face up on the patient restraint/placement portion 22, the patient 8 is restrained on the patient restraint/placement portion 22 using a dedicated restraint. Next, an image capture start position of the three-dimensional diagnostic device 18 with respect to the body of the patient 8 (the CT origin point, for example) is displayed using the horizontal direction lasers 64a and 64b, and the vertical direction laser 66, and the marks (markings) are affixed to the displayed positions 72a, 72b, and 74. Next, a contour of the affected part (the tumor, for example) is extracted from the three-dimensional image captured by the three-dimensional diagnostic device 18, and the positions of the neutron beams relating to the treatment, such as center coordinates of the affected part and the irradiation angle of the neutron beams, are determined.

Then, in accordance with the determined positions of the neutron beams, the positions of the horizontal direction lasers 64a and 64b, and the vertical direction laser 66 are changed by the control unit 60. In this way, the tumor central positions 72a, 72b, and 74 (namely, the positions 76a, 76b, and 78 at the time of the treatment using the neutron beam irradiation device 14) seen from the left-right side surface, which is orthogonal to neutron beam incident positions and irradiation axes on the body surface of the patient 8, are displayed. Marks (markings) are newly affixed to these three locations. Next, positional coordinates (x y z coordinates, for example) of the center (the tumor center, for example) of the affected part on the patient restraint/placement portion 22 relating to the diagnosis by the three-dimensional diagnostic device 18, and information relating to the posture of the patient 8 (information corresponding to the pitching angle and the rotation angle, for example) are output to the control unit 60 (the control system of the irradiation table 16). In the control unit 60, the positional coordinates of the center of the affected part on the patient restraint/placement portion 22, and the information relating to the posture of the patient 8 are stored in the non-volatile memory 604 (refer to FIG. 14).

Subsequent to the diagnosis by the three-dimensional diagnostic device 18, the patient restraint/placement portion 22, on which the patient 8 is placed and restrained, is conveyed and transferred by the conveyance device 20 from the three-dimensional diagnostic device 18 onto the top surface plate 16a of the irradiation table 16, in the state in which the patient 8 is restrained on the patient restraint/placement portion 22. First, the position of the bed 28 on the three-dimensional diagnostic device 18 in the y axis direction and the z axis direction is moved to a position for transfer, using the slide mechanism 30 and the raising/lowering mechanism 32. Next, the conveyance device 20 is moved, and the fork-shaped holding portion 52 is inserted between the groove portions 50 of the patient restraint/placement portion 22 and the bed 28. Next, the bed 28 is lowered in the z axis direction using the raising/lowering mechanism 32, and the patient restraint/placement portion 22 is in a state of being held by the holding portion 52 of the conveyance device 20. Then, the conveyance device 20 on which the patient restraint/placement portion 22 is placed is moved into the room 12 in which the neutron beam irradiation device 14 is installed. Next, coordinate values output in the diagnosis by the three-dimensional diagnostic device 18, and the offset position in the y axis direction of the patient restraint/placement portion 22 with respect to the top surface plate 16a are verified by the control unit 60. Next, the patient restraint/placement portion 22 held by the holding portion 52 is positioned above the top surface plate 16a in accordance with the verified offset position. Next, the top surface plate 16a is raised in the z axis direction by the position adjustment mechanism 34. In this way, the patient restraint/placement portion 22 is placed on the top surface plate 16a, and the protruding portions 48 and the groove portions 50 are in a state of being engaged in the offset position. Then, after the conveyance device 20 has been moved and the fork-shaped holding portion 52 has been pulled out from underneath the patient restraint/placement portion 22, the conveyance device 20 is removed (withdrawn) to the outside of the room 12.

Figure 10:
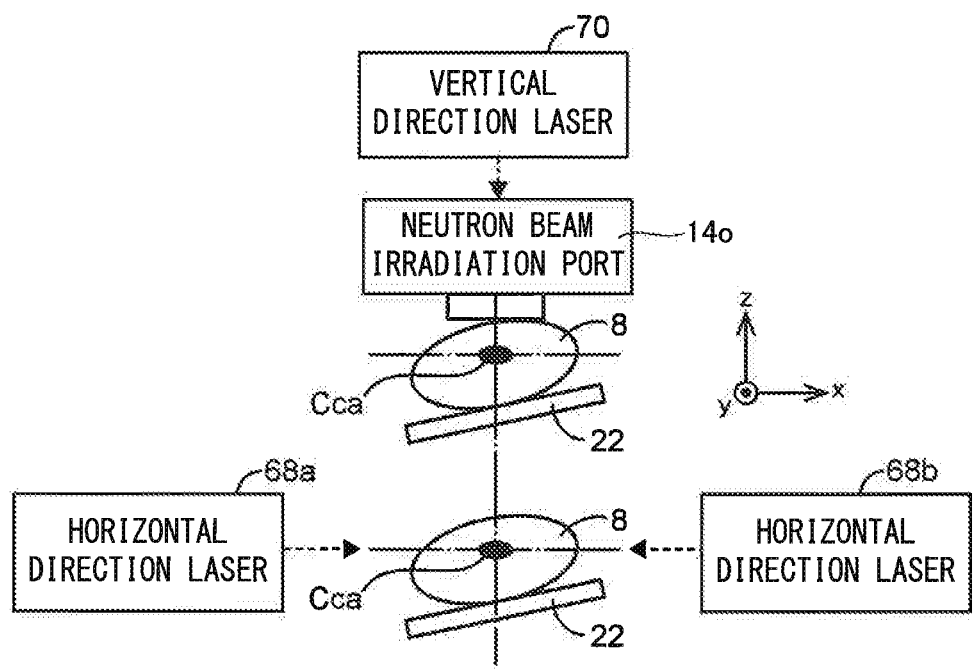
FIG. 10 is a diagram schematically showing a state of positional alignment when irradiating neutron beams using a neutron beam irradiation device provided in the therapy system shown in FIG. 1.

Following the transfer of the patient restraint/placement portion 22 to the top surface plate 16a using the conveyance device 20, on the basis of the marks (markings) affixed to the body of the patient 8, and the display positions of the horizontal direction lasers 68a and 68b, and the vertical direction laser 70, the positional alignment relating to the irradiation of the neutron beams by the neutron beam irradiation device 14 is performed. FIG. 10 is a diagram schematically showing a state of the positional alignment. First, the top surface plate 16a is moved, using the position adjustment mechanism 34 and the like, such that the imaging reference point relating to the image capture by the three-dimensional diagnostic device 18 (the CT origin point, for example) is aligned with the intersection point (hereinafter referred to as a laser pointer intersection point) between the straight line joining the display positions of the horizontal lasers 68a and 68b, and the straight line that is the straight line perpendicular to the above straight line and that passes through the display position of the vertical laser 70. Next, a comparison is made of the marks (markings) affixed in accordance with the imaging reference point, and the display positions by the horizontal direction lasers 68a and 68b, and the vertical direction laser 70, and when there is the positional displacement, the positions are adjusted by the human operation, using the position adjustment portion 62, for example. Then, on the basis of the information relating to the posture of the patient 8 output in the diagnosis by the three-dimensional diagnostic device 18, the pitching angle and a rolling angle of the top surface plate 16a with respect to the neutron beam irradiation port 14o are changed, using the first angle adjustment mechanism 36 and the second angle adjustment mechanism 38. As a result of the above positional adjustment, the top surface plate 16a is moved such that the center position of the affected part in data output to the control unit 60 is aligned with the laser pointer intersection point. Next, a comparison is made of the positions displayed on the body of the patient 8 by the horizontal direction lasers 68a and 68b, and the vertical direction laser 70, and the positions of the marks (markings) corresponding to the affected part and affixed to the body of the patient 8, and when there is positional displacement, the surgeon operates the handy terminal 605 and performs positional adjustment using the position adjustment portion 62. Specifically, the adjustment is performed using at least one of the position adjustment mechanism 34, the first angle adjustment mechanism 36, and the second angle adjustment mechanism 38, such that the error with the positions to which the marks are affixed is within the prescribed permissible range. Preferably, the center (rotational center) of the pitching angle and the rolling angle relating to this positional adjustment are used as the laser pointer intersection point.

Following the positional alignment relating to the irradiation of the neutron beams by the neutron beam irradiation device 14, the irradiation of the neutron beams by the neutron beam irradiation device 14, namely, the boron neutron capture therapy, is performed. First, when the surgeon operates the handy terminal 605 and raises the top surface plate 16a in the z axis direction through control of the position adjustment portion 62, the affected part of the patient 8 comes as close as possible to the neutron beam irradiation port 14o. Next, the handy terminal 605 is removed from the control unit 60, and the surgeon leaves (withdraws) to the outside of the room 12 with the handy terminal 605. Next, the irradiation of the neutron beams onto the affected part of the patient 8 by the neutron beam irradiation device 14 is performed. Then, the conveyance device 20 is moved into the room 12, and the top surface plate 16a is returned to the horizontal, using the first angle adjustment mechanism 36, the second angle adjustment mechanism 38, and the like. Next, the conveyance device 20 is moved to a position at which the fork-shaped holding portion 52 is inserted under the patient restraint/placement portion 22, and the top surface plate 16a is lowered in the z axis direction by the position adjustment mechanism 34. In this way, the patient restraint/placement portion 22 enters the state of being held by the holding portion 52 of the conveyance device 20. Then, the patient restraint/placement portion 22 on which the patient 8 is restrained is conveyed out of the room 12.

Below, algorithms controlling the positional alignment relating to the irradiation of the neutron beams by the neutron beam irradiation device 14 will be described in detail while referring to Expressions (1) to (13) and the like. The following description is merely an example of favorable control, and the control of the similar positional alignment may be achieved using other algorithms. First, as the treatment plan, x y z coordinates of the CT origin point and the tumor center (the center of the affected part) on the patient restraint/placement portion 22, and information relating to a treatment posture are assigned. For example, (Xct, Yct, Zct) is assigned as the coordinates of the CT origin point, (Xiso, Yiso, Ziso) is assigned as the coordinates of the tumor center), P0 is assigned as the pitching angle, R0 is assigned as the rolling angle R0, and 300×S is assigned as the y axis offset amount, and so on.

Next, conversion is performed from a coordinate system relating to the patient restraint/placement portion 22 (hereinafter referred to as a top plate coordinate system) to a coordinate system relating to the irradiation table 16 (hereinafter referred to as an irradiation table coordinate system). The origin point of the top plate coordinate system as seen from the irradiation table coordinate system is, for example, (−200, 300×S−850, 187.75). Thus, when a parallel translation of the origin point is defined in the following Expression (1) and a 90-degree rotation around the x axis, with the aim of conversion since the definition of the coordinates is different, is defined in the following Expression (2), a CT origin point M in the top plate coordinate system is expressed as in the following Expression (3) in the irradiation table coordinate system.

Expression (1)

$$T(0) = \begin{pmatrix} 1 & 0 & 0 & -200 \\ 0 & 1 & 0 & 300*S-850 \\ 0 & 0 & 1 & 187.75 \\ 0 & 0 & 0 & 1 \end{pmatrix} \quad (1)$$

Expression (2)

$$Rx(90°) = \begin{pmatrix} 1 & 0 & 0 & 0 \\ 0 & 0 & 1 & 0 \\ 0 & -1 & 0 & 0 \\ 0 & 0 & 0 & 1 \end{pmatrix} \quad (2)$$

Expression (3)

$$M = T(0)*Rx(90°)*\begin{pmatrix} Xct \\ Yct \\ Zct \\ 1 \end{pmatrix} = \begin{pmatrix} Xct-200 \\ Zct+300*S-850 \\ -Yct+187.75 \\ 1 \end{pmatrix} \quad (3)$$

Next, the movement of the top surface plate 16a to the position corresponding to the CT origin point is considered. When a height of the top surface plate 16a from the floor surface at the time of irradiation of the neutron beams by the neutron beam irradiation device 14 is 1200 mm, a laser pointer intersection point L as seen from the irradiation table coordinate system is (0, 500, 521), for example. When L is defined as in the following Expression (4), an x y z axis control target value when performing the parallel translation such that the CT origin point M is aligned with the laser pointer intersection point L is expressed by L−M. In the movement of the top surface plate 16*a* to the position corresponding to the CT origin point, the position of the top surface plate 16*a* relating to each of the axes is moved to the position corresponding to that value, by the position adjustment mechanism 34.

Expression (4)

$$L = \begin{pmatrix} 0 \\ 500 \\ 521 \\ 1 \end{pmatrix} \quad (4)$$

Next, the manual positional adjustment of the top surface plate 16*a* to the position corresponding to the CT origin point is considered. A center of rotation of the rotation angle adjustment axis 46 (hereinafter referred to as an R axis) of the top surface plate 16*a* is assumed to be the same height as the origin point, for example. A center of rotation of the pitching angle adjustment axis 44 (hereinafter referred to as a P axis) of the top surface plate 16*a* is assumed to be 118 mm vertically above the origin point, for example. Here, when C=(0, 0,118), the movement relating to each of the axes in the irradiation table coordinate system is defined in the following manner as a homogeneous transformation matrix. Specifically, when the parallel translation is defined in the following Expression (5), the R axis rotation is defined in the following Expression (6), and the P axis rotation is defined in the following Expression (7), in the manual adjustment of the CT origin point, a CT origin point Ma after applying a correction of (X1, Y1, Z1, P1, R1) is expressed in the following Expression (8). Here, an error (Ma−M) of the x y z coordinates from a planned position of the CT origin point, and the errors P1 and R1 of the angles can be mainly interpreted as errors in pattern recognition of the top plate coordinate system, or a fitting accuracy of the patient restraint/placement portion 22 and the top surface plate 16*a* (the accuracy relating to the engagement between the protruding portions 48 and the groove portions 50).

Expression (5)

$$T(X, Y, Z) = \begin{pmatrix} 1 & 0 & 0 & X \\ 0 & 1 & 0 & Y \\ 0 & 0 & 1 & Z \\ 0 & 0 & 0 & 1 \end{pmatrix} \quad (5)$$

Expression (6)

$$Ry(R) = \begin{pmatrix} \cos R & 0 & \sin R & 0 \\ 0 & 1 & 0 & 0 \\ -\sin R & 0 & \cos R & 0 \\ 0 & 0 & 0 & 1 \end{pmatrix} \quad (6)$$

Expression (7)

$$T(C)*Rx(P)*T(-C) = \begin{pmatrix} 1 & 0 & 0 & 0 \\ 0 & 1 & 0 & 0 \\ 0 & 0 & 1 & 118 \\ 0 & 0 & 0 & 1 \end{pmatrix} \begin{pmatrix} 1 & 0 & 0 & 0 \\ 0 & \cos P & -\sin P & 0 \\ 0 & \sin P & \cos P & 0 \\ 0 & 0 & 0 & 1 \end{pmatrix} \begin{pmatrix} 1 & 0 & 0 & 0 \\ 0 & 1 & 0 & 0 \\ 0 & 0 & 1 & -118 \\ 0 & 0 & 0 & 1 \end{pmatrix} \quad (7)$$

Expression (8)

$$Ma = T(-X1, -Y1, -Z1)*T(C)*Rx(P1)*T(-C)*Ry(R1)*M \quad (8)$$

Next, the movement of the top surface plate 16*a* to the position corresponding to the tumor center is considered. When a control axis origin point is (0, 0, 0, 0, 0), a tumor center N as a planned position is expressed by the following Expression (9), similarly to the CT origin point M. In the manual adjustment, as a result of moving the CT origin point by (X1, Y1, Z1, P1, R1), when the actual tumor center is positioned at the coordinates N in command data, the coordinates N corresponding to the tumor center are once more returned to the coordinates at the time of the irradiation table coordinate system, and coordinates Na of the tumor center are expressed by the following Expression (10). Next, a posture when aligning the tumor center Na with the laser pointer intersection point L, namely, coordinates Nb after rotation to the pitching angle P0+P1 and the rotation angle R0+R1, is expressed by the following Expression (11). An x y z control target value when performing parallel translation of the tumor center Nb to the laser pointer intersection point L, after the rotation relating to the P axis and the R axis, is L−Nb.

Expression (9)

$$N = T(0)*Rx(90°)*\begin{pmatrix} Xsio \\ Yiso \\ Ziso \\ 1 \end{pmatrix} = \begin{pmatrix} Xiso - 200 \\ Ziso + 300*S - 850 \\ -Yiso + 187.75 \\ 1 \end{pmatrix} \quad (9)$$

Expression (10)

$$Na = Ry(-R1)*T(C)*Rx(-P1)*T(-C)*T(-X1, -Y1, -Z1)*N \quad (10)$$

Expression (11)

$$Nb = T(C)*Rx(P0 + P1)*T(-C)*Ry(R0 + R1)*Na \quad (11)$$

Next, the manual positional adjustment of the top surface plate 16*a* to the position corresponding to the tumor center is considered. As a result of the manual adjustment, when correction of (X2, Y2, Z2, P2, R2) has been performed on the coordinates of the tumor center, a tumor center Nc after the manual adjustment is expressed in the following Expression (12). Here, an error (Nc−Nb) of the x y z coordinates of the tumor center, and errors P2 and R2 of the angles can be mainly interpreted as wobble in the position of the patient 8 in terms of a posture change with respect to the P axis and the R axis, and errors due to flexure and the like of the top surface plate 16*a*.

Expression (12)

$$Nc=T(X2, Y2, Z2)*T(C)*Rx(P0+P1+P2)*T(-C)*Ry(R0+R1+R2)*Na \quad (12)$$

In the movement of the top surface plate 16*a* to the position calculated in the manner described above, first, the top surface plate 16a is raised in the z axis direction by the position adjustment mechanism 34. A control target value relating to the raising in the z axis direction needs to be a height at which the body of the patient 8 comes as close as possible to the neutron beam irradiation port 14o, while the body of the patient 8 does not come into contact with the neutron beam irradiation port 14o. In concrete terms, when the neutron beam irradiation port 14o is 1500 mm from the floor surface, which is z=821 mm in the irradiation table coordinate system, whichever of the following is lower is set as the control target value:
(a) a position at which the tumor center Nc is 100 mm below the neutron beam irradiation port 14o; and
(b) a position at which a highest point of four corners of the patient restraint/placement portion 22 is 200 mm below the neutron beam irradiation port 14o. Preferably, the tumor center Nc is regulated by a z axis component thereof. For example, the regulation is performed such that a z axis control target value Zmax is smaller than a value obtained by subtracting the z axis component of Nc from 721, namely, Zmax<721−(z axis component of Nc). The tumor center Nc is regulated by a maximum point of the four corners of the patient restraint/placement portion 22. For example, when at the origin point, coordinates A of the four corners are (±230, ±1000+300×S, 281), and coordinates Aa after the rotation of a P angle and an R angle are expressed in the following Expression (13). The z axis control target value Zmax is regulated such that Zmax is smaller than a value obtained by subtracting a highest point of the z components of the four coordinates Aa from 621, namely, Zmax<621−(highest point of z components of four coordinates Aa).

Expression (13)

$$Aa = T(C)*Rx(P)*T(-C)*Ry(R)*A \quad (13)$$

After the top surface plate 16a has been moved by the position adjustment mechanism 34 in the above-described manner, the manual positional adjustment of the top surface plate 16a is performed using the position adjustment portion 62, and the position of the top surface plate 16a with respect to the neutron beam irradiation port 14o, and the posture of the patient 8 restrained on the patient restraint/placement portion 22 are finally determined. For example, by the manual operation by the surgeon, the top surface plate 16a is raised as far as a position at which the body of the patient 8 comes as close as possible to the neutron beam irradiation port 14o. In addition, the positional adjustment is performed in the three axial directions and in the rotational directions around the P axis and the R axis, and the posture of the patient 8 restrained on the patient restraint/placement portion 22 is finally determined. As a result of this manual operation, correction of (X3, Y3, Z3, P3, R3) is performed.

In the above-described control, preferably, information relating to the control is stored as a log in a storage portion provided in the control unit 60. For example, data read into a predetermined storage medium, the manual adjustment values (X1, Y1, Z1, P1, R1) of the CT origin point, the manual adjustment values (X2, Y2, Z2, P2, R2) of the tumor center, the final adjustment values (X3, Y3, Z3, P3, R3), and information about a date, time, and the like at which each of the steps of the position determining procedure are performed are stored.

Figure 13:
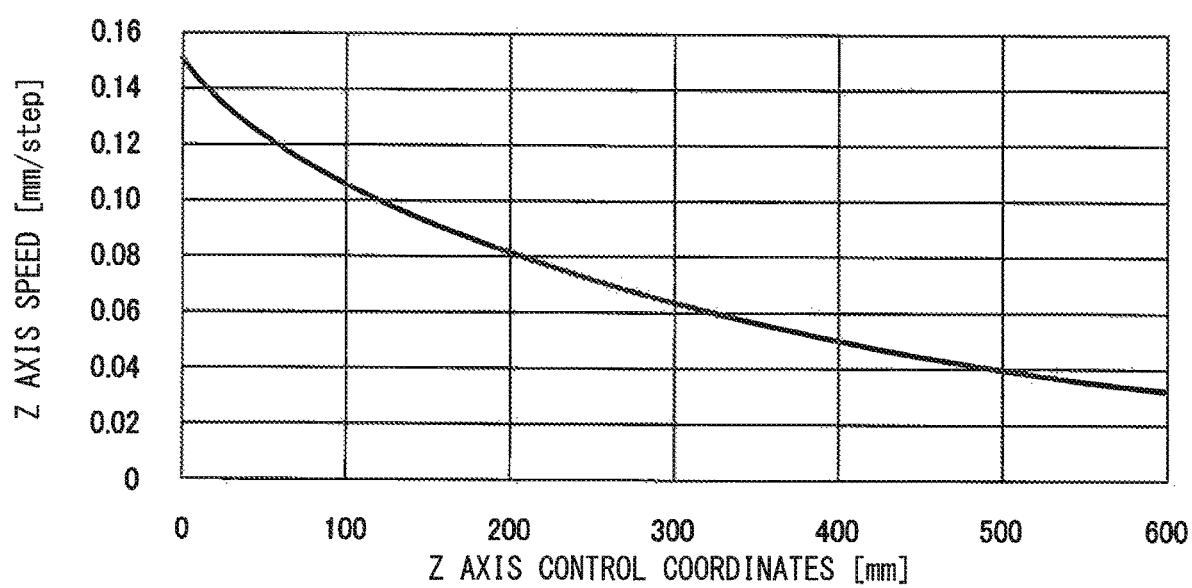
FIG. 13 is a diagram illustrating, in the positional adjustment of the irradiation table, z axis coordinates and a z axis direction speed when a step amount in the y and z axis directions is constant.

FIG. 11 is a diagram illustrating a movement speed of each of portions relating to the positional adjustment of the top surface plate 16a, and FIG. 12 is a diagram illustrating a number of pulses of each of the portions relating to the positional adjustment of the top surface plate 16a, respectively. FIG. 13 is a diagram illustrating, in the positional adjustment of the top surface plate 16a, z axis coordinates and a z axis direction speed when a step amount in the y and z axis directions is constant. As shown in FIG. 13, in the movement in the z axis direction, given the device dimensions of the top surface plate 16a of the above-described embodiment, a raising and lowering speed corresponding to the movement of the y and z axes is approximately 4-fold different between the top and the bottom of a movable range, even when using the same motor rotation speed. During the z axis movement, a ratio of a manner of moving the first YZ axis motor 624 and the second YZ axis motor 626 (a rotation amount ratio) is constant. This ratio depends on the structure and dimensions of the y z axis movement arm 40. When the y and z axis speeds are constant irrespective of a height in the z axis direction, at the height at which the body of the patient 8 is in the vicinity of the laser pointer intersection point (z=200 mm, for example), the pulse number is set such that these speeds are close to that of the other axes. With respect to the movement in the z axis direction, when the setting of the number of pulses for yz1 and yz2 is set as a ratio of 1:α expressed by integers, a y axis movement amount resulting from an accumulation error is small. For example, yz1:yz2=37:237 is an optimum ratio. In the automatic raising and lowering operation in the transfer of the top surface plate 16a and the conveyance device 20, since a movement in the z axis direction is required to be at a relatively slow speed, the speed is assumed to be approximately ⅓ the movement speed in the z axis direction of the other positional adjustments. In this way, as the movement speed and the number of pulses of each of the parts relating to the positional adjustment of the top surface plate 16a, favorable values such as the values shown in FIG. 11 and FIG. 12 are set.

Figure 23:
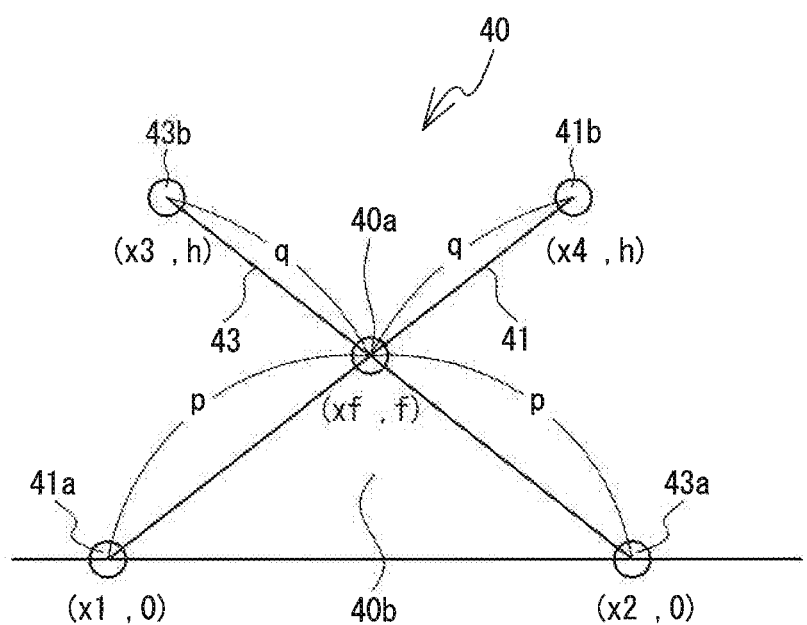
FIG. 23 is a schematic diagram depicting control of a y z axis movement arm 40.

Next, operation methods of a first YZ axis arm 41 and a second YZ axis arm 43 that configure the YZ axis arm 40 will be described with reference to FIG. 23. In FIG. 23, each of the arms is illustrated in a simplified manner using lines. As shown in FIG. 23, the first YZ axis arm 41 and the second YZ axis arm 43 are connected at a separation point 40a by which each of the first YZ axis arm 41 and the second YZ axis arm 43 are divided at a ratio of q:p. The first YZ axis motor 624 controls the first YZ axis arm 41, and the second YZ axis motor 626 controls the second YZ axis arm 43. As a basic operation, a method will be described in which a height, namely, h, is raised and lowered without changing a central position of an upper structural portion loaded on a point 41b (x4, h) of an upper end of the first YZ axis arm 41 and a point 43b (x3, h) of an upper end of the second YZ axis arm 43.

First, from the scaling law for triangles:

Expression (14)

$$x4 - x3 = \frac{q}{p}(x2 - x1) \quad \text{A}$$

Then, since the x direction coordinates of a center point of a point 41a (x1, 0) and a point 43a (x2, 0) of the lower ends of each of the arms matches a center point of the two $$x1 + x2 = x3 + x4 \quad \text{B}$$

upper points:
Expression (15)
If x3 and x4 are solved when Expression A and Expression B are simultaneously established, then:

Expression (16)

$$x3 = \frac{(q-p)x2 - (q+p)x1}{2p},$$

$$x4 = \frac{(q+p)x2 + (p-q)x1}{2p}$$

The raising and lowering without changing the center of the upper structure means that on the device structure, h is moved without changing x3. Thus, when movement amounts by the first YZ axis motor 624 and the second YZ axis motor 626 are Δ1 and Δ2, respectively, this becomes an identical equation in which a numerator of x3 is identically placed as "zero", and thus:

Expression (17)

$$(q-p)\Delta 2 - (q+p)\Delta 1 = 0,$$

$$\Delta 1 = \frac{(q-p)}{(q+p)}\Delta 2$$

As in the above Expression (17), by constantly moving Δ1 and Δ2 at the ratio of the above Expression (17), the center position of the upper structure can be maintained to be the same.

Next, control of a height movement speed will be described. If Pythagoras' theorem is applied to a lower triangle 40b formed by the separation point 40a of the first YZ axis arm 41 and the second YZ axis arm 43, the point 41a, and the point 43a, then:

$$(x-xf)^2 + f^2 = (x2-xf)^2 + f^2 = p^2 \quad \text{Expression (18)}$$

As in the above equation, $$f^2 = p^2 - (x2-xf)^2 = p^2 - (x1-xf)^2$$

By assigning $$xf = \frac{x1 + x2}{2}$$

into the above equation and sorting out, $$f = \sqrt{p^2 - \left(\frac{x2-x1}{2}\right)^2}$$

As in Law of similarity, $$h = \frac{p+q}{p}f$$

$$h = \frac{p+q}{p}\sqrt{p^2 - \left(\frac{x2-x1}{2}\right)^2}$$

$$\frac{x2-x1}{2} \equiv L.$$

By differentiating the above h with L, $$\frac{dh}{dL} = -\frac{(q+p)L}{p\sqrt{p^2 - L^2}}$$

By the above calculation, it can be seen that the speed changes significantly depending on L. Further, the change of speed is not determined by positions of x1 and x2, but by a distance between x1 and x2.

According to the present embodiment, since the therapy system 10 is provided with the patient restraint/placement portion 22 that restrains the patient 8 placed thereon, the three-dimensional diagnostic device 18 that detects the position of the affected part in the patient 8, the top surface plate 16a whose position is determined with respect to the neutron beam irradiation device 14, the position adjustment mechanism 34 that changes the position of the top surface plate 16a with respect to the neutron beam irradiation port 14o of the neutron beam irradiation device 14 in the respective directions of the three axes that are orthogonal to each other, and the control unit 60, which aligns the position of the affected part of the patient 8 detected by the three-dimensional diagnostic device 18 with the position of the neutron beams irradiated from the neutron beam irradiation device 14, by using the position adjustment mechanism 34 to change the position, in the directions of each of the three axes, of the top surface plate 16a onto which the patient restraint/placement portion 22 has been transferred, and which also causes the affected part to come as close as possible to the neutron beam irradiation port 14o, demands unique to boron neutron capture therapy can be sufficiently fulfilled. Specifically, the boron neutron capture therapy system 10 can be provided that performs position determining with sufficient accuracy at the time of the boron neutron capture therapy.

Since the therapy system 10 is provided with the conveyance device 20 as a transfer device to transfer the patient restraint/placement portion 22 on which the patient 8 is placed and restrained between the three-dimensional diagnostic device 18 and the top surface plate 16a, sufficiently accurate position determination can be performed as well as achieving the simple transfer at the time of the boron neutron capture therapy.

When detecting the position of the affected part using the three-dimensional diagnostic device 18, since the therapy system 10 is provided with the position adjustment portion 62 that aligns the position of the affected part of the patient 8 detected by the three-dimensional diagnostic device 18, and the position of the neutron beams irradiated by the neutron beam irradiation device 14, by using the position adjustment mechanism 34 to change the position relating to the directions of each of the three axes of the top surface plate 16a onto which the patient restraint/placement portion 22 has been transferred, on the basis of the marks corresponding to the positional coordinates relating to the detection that are affixed to the patient 8 placed and restrained on the patient restraint/placement portion 22, simple and sufficiently accurate position determination can be performed at the time of the boron neutron capture therapy.

Since the therapy system 10 is provided with the first angle adjustment mechanism 36 that changes the angle of the top surface plate 16a with respect to the irradiation direction of the neutron beams around an axis that is parallel to one of the axes among the three axes, and the second angle adjustment mechanism 38 that changes the angle of the top surface plate 16a with respect to the irradiation direction of the neutron beams around an axis that is parallel to a different one of the axes among the three axes, the position determination relating to the boron neutron capture therapy can be performed simply and with a high degree of accuracy.

Since the patient restraint/placement portion 22 and the top surface plate 16a are provided with the protruding portions 48 and the groove portions 50, as the engagement structure, on sections that are caused to face each other and be engaged with each other when the patient restraint/placement portion 22 is transferred onto the top surface plate 16a, the position of the patient restraint/placement portion 22 with respect to the top surface plate 16a can be determined easily and with a high degree of accuracy.

The three-dimensional diagnostic device 18 is a device that captures an image of the inside of the body of the patient 8, and, as the material of the marks, a material is used that allows sufficient distinction between the main material of the patient restraint/placement portion 22 and the marks in the image captured by the three-dimensional diagnostic device 18. Thus, at the time of the boron neutron capture therapy, the position determination can be performed in an easy and practical manner.

As the transfer device, the therapy system 10 is provided with the conveyance device 20 that conveys the patient restraint/placement portion 22 in a state in which the patient restraint/placement portion 22 is placed on the conveyance device 20. The conveyance device 20 is provided with the holding portion 52 that holds the patient restraint/placement portion 22 and that can be pulled out after transferring the patient restraint/placement portion 22 onto the three-dimensional diagnostic device 18 or onto the top surface plate 16a, and the raising/lowering mechanism provided in the conveyance device 20, the raising/lowering mechanism 32 provided in the three-dimensional diagnostic device 18, or the position adjustment mechanism 34 is used to transfer the patient restraint/placement portion 22 on which the patient 8 is restrained between the conveyance device 20 and the three-dimensional diagnostic device 18 or the top surface plate 16a. Thus, the patient restraint/placement portion 22 on which the patient 8 is restrained can be transferred between the conveyance device 20 and the three-dimensional diagnostic device 18 or the top surface plate 16a in an easy and practical manner.

The therapy system 10 is provided with the horizontal direction lasers 64a and 64b, and the vertical direction laser 66 that function as the position display portion and perform the display in order to verify, on the basis of the display by the position display portion, that the position of the affected part of the patient 8 detected by the three-dimensional diagnostic device 18 is sufficiently aligned with respect to the position of the neutron beams irradiated from the neutron beam irradiation device 14, and is provided with the position adjustment portion 62 that performs the adjustment using at least one of the position adjustment mechanism 34, the first angle adjustment mechanism 36, and the second angle adjustment mechanism 38, such that the error between the position of the affected part of the patient 8 detected by the three-dimensional diagnostic device 18 and the position of the neutron beams irradiated from the neutron beam irradiation device 14 is within the prescribed permissible range. Thus, the position determination relating to the boron neutron capture therapy can be performed in an easy and practical manner.

The position display portion performs the display to verify that the imaging reference point of the image by the three-dimensional diagnostic device 18 is sufficiently aligned with respect to the coordinate system corresponding to the directions of the three axes. Since the position adjustment portion 62 performs the adjustment, on the basis of the display by the position display portion, such that the error of the imaging reference point of the image by the three-dimensional diagnostic device 18 with respect to the coordinate system corresponding to the directions of the three axes of the top surface plate 16a is within the prescribed permissible range. Thus, the position determination relating to the boron neutron capture therapy can be performed in an easy and practical manner.

The top surface plate 16a is configured from the material ensuring that the maximum exposure per hour of the employee is 20 mSv or less when the top surface plate 16a is radioactivated by the neutron beams irradiated from the neutron beam irradiation device 14. Thus, as the material of the top surface plate 16a, a material is used that is not easily radioactivated, or if radioactivated, can suppress that radioactivity to a sufficiently small value. As a result, the exposure of the patient 8 and medical employees can be suppressed as much as possible.

<Collision Avoidance Processing>

Figure 15:
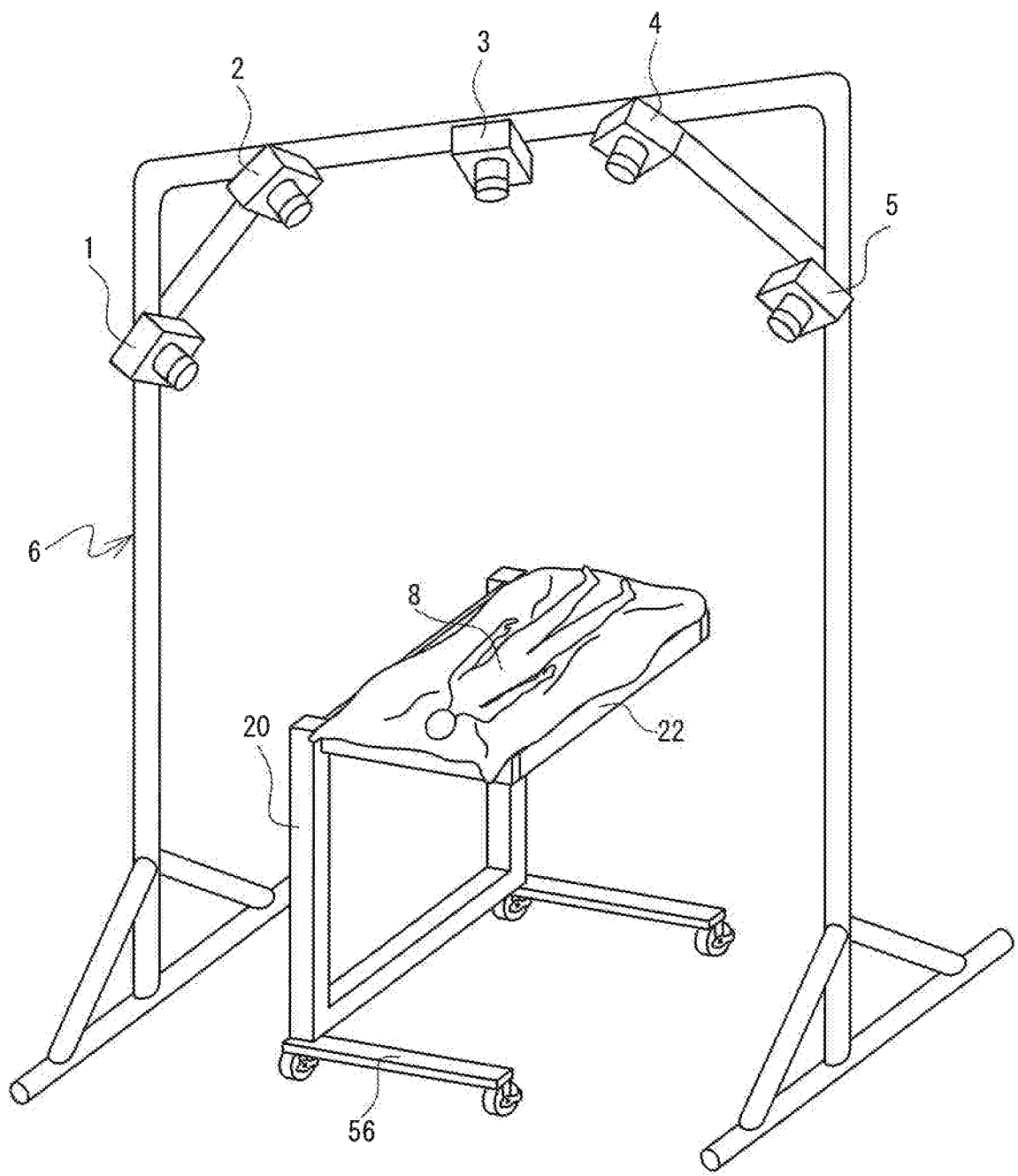
FIG. 15 is a perspective view showing a state in which photographs of a patient 8 and a patient restraint/placement unit 22 are captured by cameras 1 to 5 attached to an aluminum camera frame 6.

Next, collision avoidance processing that prevents mistaken contact of the body of the patient 8 with the irradiation port 14o will be described. In the collision avoidance processing, the CPU 601 calculates a movable range of a trajectory of three-dimensional data of a contour of a surface of the body of the patient 8, using simulation, and software limit processing is performed to change the movement of the top surface plate 16a. Specifically, the collision avoidance processing measures, three-dimensionally, the shape of the contour of the body of the patient 8 restrained on the patient restraint/placement portion 22, estimates a spatial position of the contour of the body of the patient 8 in accordance with the movement of the irradiation table 16, and performs the collision avoidance processing. If information can be obtained in advance as to the height of the surface of the body of the patient 8 from the top surface plate 16a, when the top surface plate 16a is raised in the z axis direction, the moveable range of the top surface plate 16a can be limited so as to prevent mistaken contact of the body surface of the patient 8 with the neutron beam irradiation port 14o that is present immediately above the part to be treated, before such contact happens. As means of obtaining the three-dimensional data of the contour of the body surface of the patient 8, the three-dimensional data of the contour of the body surface of the patient 8 is obtained using images from the plurality of optical cameras 1 to 5, as shown in FIG. 15. As an example, the cameras 1 to 5 are provided on an upper portion of the aluminum camera frame 6. As an example, the five cameras 1 to 5 disposed in a circular arc at a height of 2.5 m from the floor are installed. As an example of the cameras 1 to 5, digital single lens reflex cameras can be used. In the collision avoidance processing, the contour of the body surface of the patient 8 is calculated by three-dimensionally reconfiguring images captured from a plurality of angles of the patient 8 restrained on the patient restraint/placement portion 22, using stereo camera principles.

Image Capture of Patient 8 and Patient Restraint/Placement Portion 22

Figure 16:
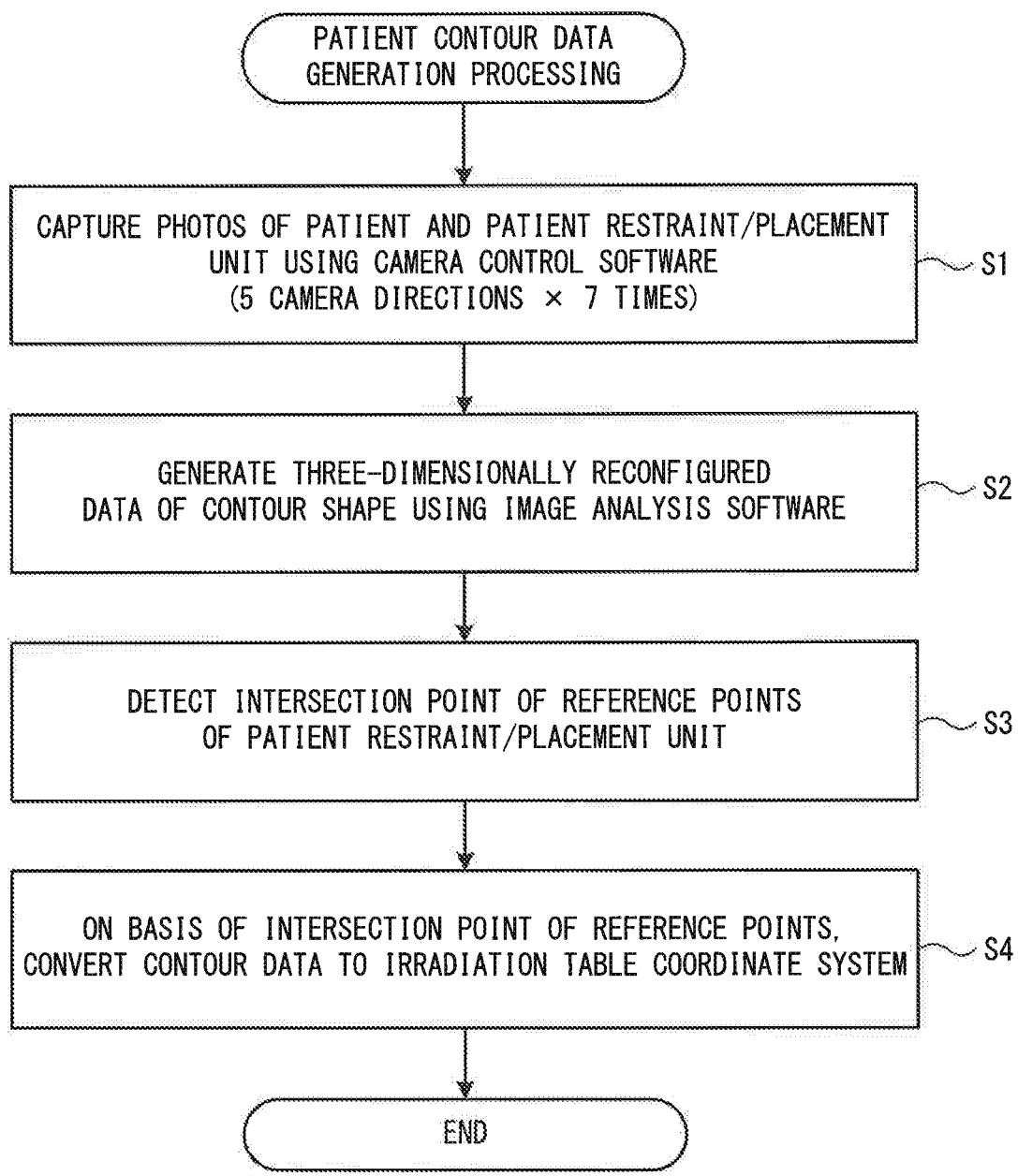
FIG. 16 is a flowchart of patient contour data generation processing.

Next, generation processing of the contour data of the patient 8 will be described with reference to the flowchart shown in FIG. 16. First, the CPU 601 of the control unit 60 reads out camera control software stored in the ROM 602, controls the cameras 1 to 5, performs image capture seven times while moving the conveyance device 20 on which the patient 8 is placed in the head to toe direction, and obtains a total of 35 high definition images (step S1).

Generation of three-dimensional reconfigured data of body of patient 8 Three-dimensional data of the body of the patient 8 is generated by three-dimensionally reconfiguring the 35 high definition images captured in the processing at step S1 (step S2). More specifically, the CPU 601 of the control unit 60 reads out image analysis software stored in the ROM 602, and, on the basis of the 35 high definition images obtained in the processing at step S1, performs generation of three-dimensional data by three-dimensionally reconfiguring the contour shape using the image analysis software (step S2). Examples of the image analysis software include Photoscan (registered trademark) made by Agisoft. The three-dimensional data of the patient 8 output by Photoscan (registered trademark) is three-dimensional point group data including RGB information in the ply format.

<Detection of Intersection Point of Reference Points of Patient Restraint/Placement Portion 22>
(Definition of Reference Points of Patient Restraint/Placement Portion 22)

Figure 17:
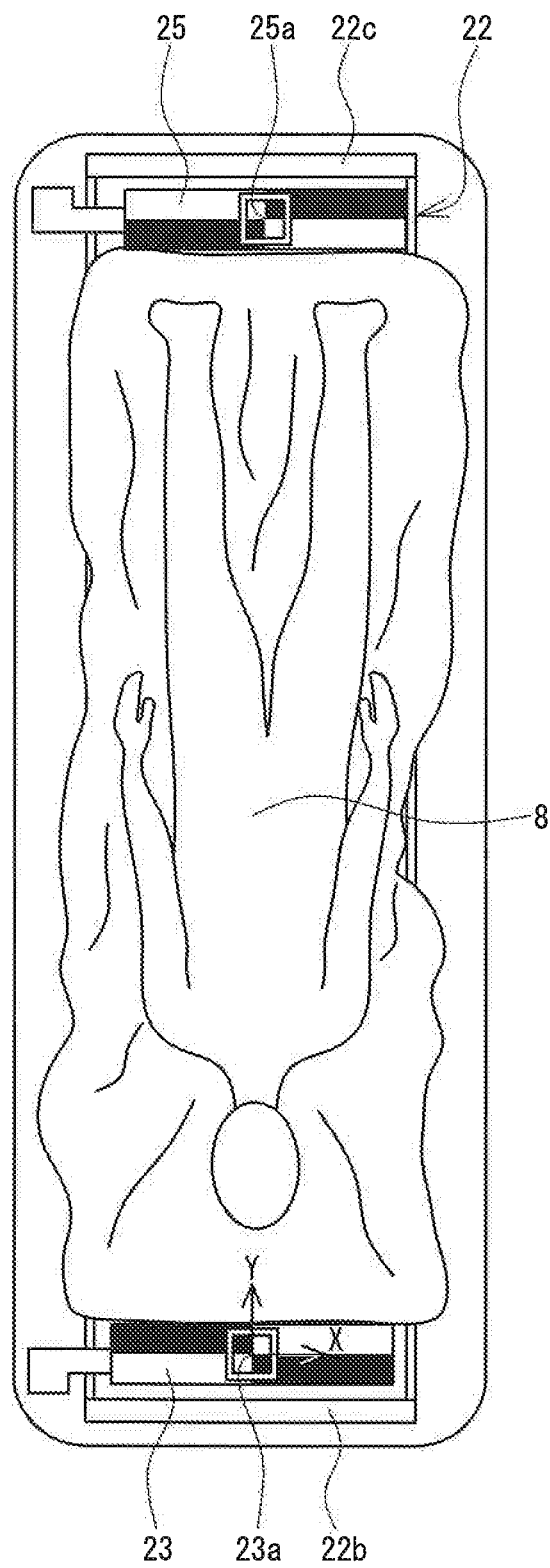
FIG. 17 is a plan view of the patient restraint/placement unit 22.

A handle 22b and a handle 22c are provided, respectively, on both the ends, in a Y direction, of the patient restraint/placement portion 22 shown in FIG. 17. A reference plate 23 shown in FIG. 18 and FIG. 19 that is rectangular in a plan view is provided on the upper surface of the handle 22b. A reference plate 25 that is rectangular in a plan view is also provided on the upper surface of the handle 22c. The reference plate 23 is a black and white checkered pattern, and an intersection point of the black and white checkered pattern is a reference point 23a. A range indicated by a circle 23b shown using a dotted line (refer to FIG. 18 and FIG. 19) is an assumed range of the presence of the intersection point. The reference plate 25 is also a black and white checkered pattern, and an intersection point of the black and white checkered pattern is a reference point 25a. In processing at step S3, the reference point 23a and the reference point 25a are detected as reference points of the coordinate system of the patient restraint/placement portion 22 (step S3).

The CPU 601 of the control unit 60 reads out image recognition software stored in the ROM 602, and detects the reference point 23a and the reference point 25a of the patient restraint/placement portion 22 (step S3). As an example, the following type of processing is performed. A pitch of the reference point 23a and the reference point 25a is 1915 mm. It is assumed that positional coordinate information of the plurality of cameras is set in advance in the image analysis software, using the ground control function of Photoscan (registered trademark), and that the reference point 23a is captured while accuracy is always stable at approximately ±20 mm in the coordinate system of the reconfigured contour data of the patient 8, taking the position coordinate information as a reference. The ground control function is set such that the X, Y coordinates of the reference point 23a are (0, 0). Based on this assumption, the reference points on the contour data of the patient 8 are always within the following X, Y coordinate range:
Reference point 23a: (−20, −20)<(X, Y), <(+20, +20)
Reference point 25a: (−20, +1935)<(X, Y), <(+20, +1895)
(Conversion of RGB Color Information to Grey Scale)

Next, the CPU 601 takes a simple mean value of the RGB values, in order to determine, using grey scale, the black and white contrast of the checkered pattern of the reference plate 23 and the reference plate 25.

$$Grey=(R+G+B)/3$$

Thus, each of point groups of the contour data of the patient 8 becomes a set of the values (X, Y, Z, Grey).

(Edge Detection in Y Direction of Reference Point 23a)

Figure 18:
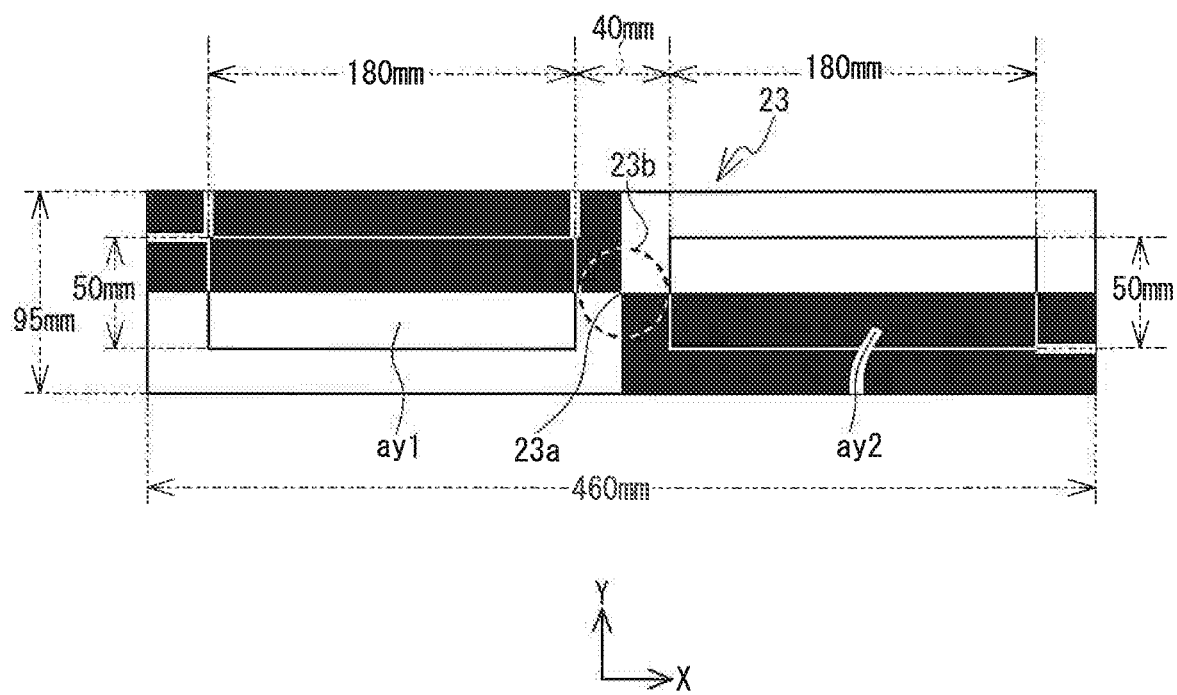
FIG. 18 is a plan view of a reference plate 23.

Next, the CPU 601 extracts, from the contour data of the patient 8, only points that are in a range [ay1] shown in FIG. 18. It is necessary for the size and the position of the range [ay1] to have a dimension in the X direction of 40 mm or more, so that even if the position of the reference plate 23 is displaced by ±20 mm, an edge in the Y direction falls within the range [ay1]. Further, so that extra parts of the image other than the edge in the Y direction are not included in the range [ay1], it is necessary for the range [ay1] to be disposed providing a distance of 20 mm or more from the outer shape of the reference plate 23 and from the reference point 23a. In the present embodiment, the range [ay1] is preferably defined in the following coordinate area:
[ay1]: (−200, −25)<(X, Y), <(−20, +25)

Next, the CPU 601 performs an ascending sort of the Y coordinate values of the point group data [ay1] extracted from the contour data. The CPU 601 assigns a reference symbol i to the data order (i=1, 2, . . . n). The CPU 601 calculates an average value White of the Grey values from the first to the i-th data array. In the same manner, the CPU 601 calculates an average value Black of the Grey values from the i+1-th to the n-th data array. When i is changed from 1 to n−1, the CPU 601 determines that there is the edge from black to white at the i-th point at which the difference between White and Black is largest. In this way, a Y coordinate value of a k-th point is used as a Y coordinate aY1 of the edge. Similarly, the CPU 601 determines the edge from white to black for a range [ay2] shown in FIG. 18, and uses the edge from white to black as a Y coordinate aY2 of the edge. The CPU 601 sets an average value of the detected two edges as the Y coordinate of the reference point 23a.

$$aY=(aY1+aY2)/2$$

(Edge Detection in X Direction of Reference Point 23a)

Figure 19:
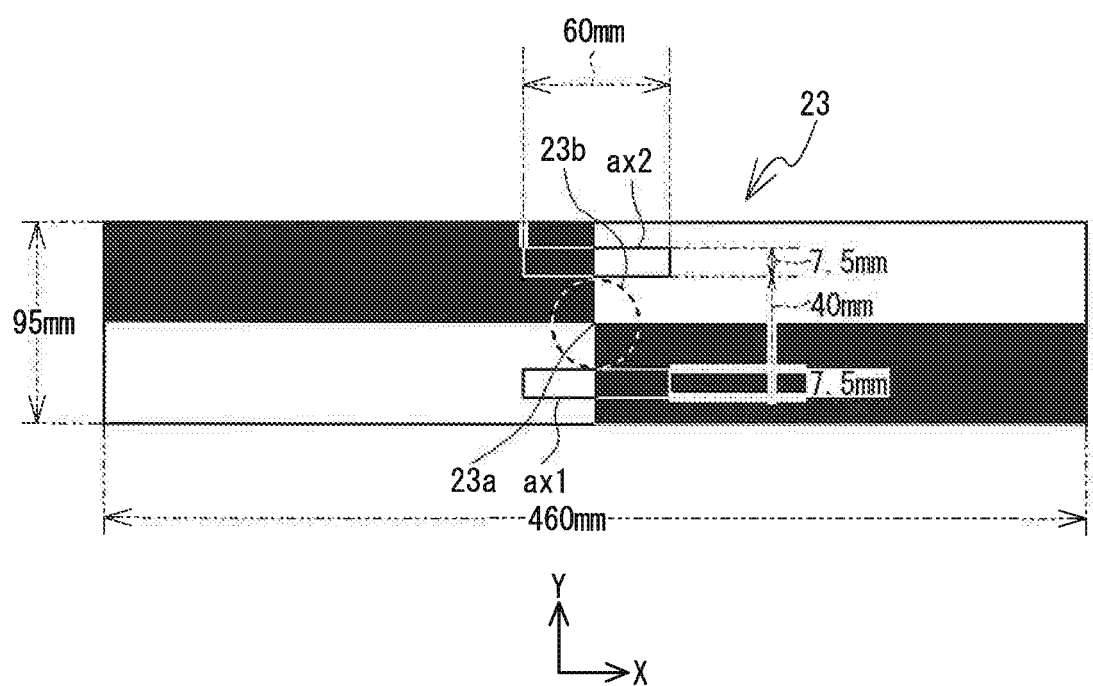
FIG. 19 is a plan view of the reference plate 23.

The CPU 601 extracts, from the contour data of the patient 8, only points that are in a range [ax1] shown in FIG. 19. From the same viewpoint as for the ranges [ay1] and [ay2], it is necessary for the size and the position of the range [ax1] to be defined such that even if the position of the reference plate 23 is displaced by ±20 mm, only an edge in the X direction is within the range [ax1].
[ax1]: (−30, −27.5)<(X, Y), <(+30, −20)
The CPU 601 performs an ascending sort of the X coordinate values of the extracted point group data [ax1]. In the same manner as for the Y coordinates, the CPU 601 detects X coordinates aX1 and aX2 of the edges of two areas [ax1] and [ax2]. The CPU 601 sets an average value of the detected two edges as the X coordinate of the reference point 23a. aX=(aX1+aX2)/2

(Detection of Z Coordinates of Reference Point 23a)

Since there is a tendency for a height of the Z coordinates of the reference point 23a to be output slightly differently in a white area and a black area, it is necessary to calculate the average value of the Z coordinates of an area in which the ratio of each of white and black is the same. The average value of the Z coordinates of a point group of the following area [az] is a Z coordinate aZ of a reference point a.
[az]: (aX−20, aY−20)<(X, Y), <(aX+20, aY+20)
aZ=Average (Z coordinates of [az])

(Detection of Reference Point 25a)

The CPU 601 detects the X, Y, and Z coordinate values of the reference point 25a of the reference plate 25 in the same manner as for the reference point 23a.

<Conversion of Coordinates to Irradiation Table Coordinate System>

In order to match all the points of the contour data of the patient 8 with the irradiation table coordinate system, the CPU 601 performs coordinate conversion including rotation/parallel movement/enlargement and reduction, such that the reference point 23a=(0, −957.5, +281), and the reference point 25a=(0, +957.5, +281) (step S4). This is described in detail below.

(Definition of Irradiation Table Coordinate System)

An example of the irradiation table coordinate system is defined as below.

The origin point of the X axis and the Y axis is the center of the patient restraint/placement portion 22

The origin point of the Z axis is 187.5 mm below the origin point of the X axis and the Y axis (679 mm up from the floor, 281 mm below the top surface of the handle 22b and the handle 22c of the patient restraint/placement portion 22)

The rotation center of the pitching angle is 118 mm up from the origin point of the X axis and the Y axis The rotation center of the rolling angle is the same as the origin point of the X axis and the Y axis (Scale Conversion Using Distance Between Two Detected Reference Points)

As a design value, the reference point 23a and the reference point 25a shown in FIG. 17 are separated by 1915 mm in the Y direction. When the coordinate value of the reference point 23a detected in the original data of the contour of the patient 8 is a=(aX, aY, zZ), and the coordinate value of the reference point 25a is b=(bX, bY, bZ), the CPU 601 calculates the distance |b−a| between the reference point 23a and the reference point 25a, and, by multiplying the original coordinate values by (1915/|b−a|), matches the contour date of the patient 8 to the actual patient 8.

(Taking Straight Line Joining Two Detected Reference Points as Y Axis Vector)

The CPU 601 calculates a unit vector of the Y axis in the irradiation table coordinate system using Y=(b−a)/|b−a|.

(Calculation of Unit Vector of Z Axis Using Plane in Vicinity of Two Reference Points)

For the unit vector of the Z axis in the irradiation table coordinate system, the CPU 601 uses the least squares method to calculate a regression place surface from the point group data of a periphery of the reference point 23a (aX±200, aY±25 mm) and a periphery of the reference point 25a (bX±200, bY±25 mm). Note here that, given a condition that the unit vector Z of the Z axis is orthogonal to the above unit vector Y of the Y axis, an inner product (Y/Z)=0 is added.

(Calculation of Unit Vector of X Axis Orthogonal to Two Unit Vectors of Y and Z)

The CPU 601 calculates the X axis unit vector relating to the irradiation table coordinate system, using an outer product (Y×Z).

(Rotation of Contour Data to Irradiation Table Coordinate System)

Using the unit vectors X, Y, and Z of the irradiation table coordinate system calculated as above, the CPU 601 rotates each of points of the contour data. A transformation matrix is performed using the following Expression.

Expression (19)

$$\text{Rotation:} R = \begin{pmatrix} X^T \\ Y^T \\ Z^T \end{pmatrix}$$

A rotation operation is performed on each of contour points N as a result of the calculation of the above Expression. Each of the contour points after the rotation is expressed by (R*N).

(Parallel Translation of Contour Data to Irradiation Table Coordinate System)

The CPU 601 performs parallel translation such that a midpoint between the reference point 23a and the reference point 25a (a+b)/2 after the above rotation conversion is matched up with the irradiation table coordinate system O=(0, 0, 281). Each of the contour points after the parallel translation is expressed by (R*N−(a+b)/2+O). By the above-described operation, the contour data of the patient 8 obtained from Photoscan (registered trademark) is caused to match the irradiation table coordinate system, and can be used in the determination by collision avoidance means (step S4). By the above-described processing, the patient 8 contour data generating processing is performed.

<Definition of Irradiation Port 14o>

As an example, the irradiation port 14o shown in FIG. 10 has a cylindrical shape with a diameter of 1, 400 mm, and is suspended such that the bottom surface of the cylindrical shape is at a height of 1, 500 mm from the floor. During use, a lid of the irradiation port 14o attached to the bottom surface is retracted by being swung to the outside of an operation range of the irradiation table. In the irradiation table coordinate system, a space satisfying:

$X^2+(Y-500)^2 \leq 1400^2$ and $Z \geq (1500-679)=821$ is a prohibited area. When using the automatic mode operation for the collision determination in actuality, an additional space of 50 mm in the horizontal direction and 50 mm in the vertical direction is secured with respect to the above area, and a space satisfying the following conditional expressions:

$X^2+(Y-500)^2 \leq 1450^2$ and $Z \geq 771$ is the prohibited area.

In the above-described embodiment, since the Z origin point in the irradiation table coordinate system is 679 mm from the floor, a height limit of the irradiation table coordinate system is 821 mm. Taking an additional 50 mm allowance from there is the reason for the height limit of 771 mm in the Z axis direction. Thus, Z≥771 becomes the height limit. If the irradiation table coordinate system is not used, and the height limit from the floor is simply determined, 50 mm may be subtracted from 1500 mm, and the height limit in the Z axis direction may be 1450 mm.

<Irradiation Table Movement Processing>

Next, irradiation table movement processing, which performs the collision avoidance processing using position estimation of the patient 8, will be described with reference to FIG. 20. The CPU 601 of the control unit 60 reads, from the non-volatile memory 604, target coordinates of an automatic position determining operation (step S11). The target coordinates of the automatic position determining operation are stored in advance in the non-volatile memory 604. The CPU 601 determines whether a value of the Z coordinate of a highest point of the contour patient 8, in the target coordinates read from the non-volatile memory 604, exceeds the height limit (Z≥771) (step S12). When it is determined that the Z coordinate of the highest point of the contour of the patient 8 in the target coordinates exceeds the height limit (yes at step S12), the CPU 601 decreases the target coordinate of the Z axis by the amount by which the highest point of the contour of the patient 8 exceeds the height limit (step S13).

When it is determined that the Z coordinate of the highest point of the contour of the patient 8, of the target coordinates, does not exceed the height limit (no at step S12), the CPU 601 divides a movement of the top surface plate 16a from the current coordinates of the top surface plate 16a to the target coordinates read at step S11 (the X axis movement, the Y axis movement, the Z axis movement, the pitching angle rotation, the rolling angle rotation) into 100 equal parts, and calculates a trajectory of the contour of the patient 8 when the movement advances in each of 1 interval (step S14).

The calculation of the trajectory of the contour of the patient 8 (step S14) is performed in the following manner. In the irradiation table coordinate system, when coordinates of an N-th trajectory point of the contour data point group of the patient 8 are denoted by N, N is as follows:

Expression (20)

$$N = \begin{pmatrix} Nx \\ Ny \\ Nz \\ 1 \end{pmatrix}$$

The positions of the above contour points are calculated when control coordinate values of the irradiation table are (X, Y, Z, P, R). P indicates the pitching angle rotation, and R indicates the rolling angle rotation. First, the parallel translation of the X, Y, and Z axes, and a simultaneous transformation matrix for the pitching rotation and the rolling rotation relating to each of the control coordinate values are defined as follows:

Expression (21)

$$\text{Parallel translation}: T(X, Y, Z) = \begin{pmatrix} 1 & 0 & 0 & X \\ 0 & 1 & 0 & Y \\ 0 & 0 & 1 & Z \\ 0 & 0 & 0 & 1 \end{pmatrix}$$

Expression (22)

$$R \text{ axis rotation}: Ry(R) = \begin{pmatrix} \cos R & 0 & \sin R & 0 \\ 0 & 1 & 0 & 0 \\ -\sin R & 0 & \cos R & 0 \\ 0 & 0 & 0 & 1 \end{pmatrix}$$

Expression (23)

$$P \text{ axis rotation}: T(C) * Rx(P) * T(-C) =$$

-continued $$\begin{pmatrix} 1 & 0 & 0 & 0 \\ 0 & 1 & 0 & 0 \\ 0 & 0 & 1 & 118 \\ 0 & 0 & 0 & 1 \end{pmatrix} \begin{pmatrix} 1 & 0 & 0 & 0 \\ 0 & \cos P & -\sin P & 0 \\ 0 & \sin P & \cos P & 0 \\ 0 & 0 & 0 & 1 \end{pmatrix} \begin{pmatrix} 1 & 0 & 0 & 0 \\ 0 & 1 & 0 & 0 \\ 0 & 0 & 1 & -118 \\ 0 & 0 & 0 & 1 \end{pmatrix}$$

A contour point N' after the movement (X, Y, Z, P, R) has been performed with respect to the contour point N is expressed as follows:

$$N' = T(-X, -Y, -Z) * T(C) * Rx(P) * T(-C) * Ry(R) * N \quad \text{Expression (24)}$$

Namely, N' is expressed as follows:

Expression (25)

$$N' = \begin{pmatrix} N'x \\ N'y \\ N'z \\ 1 \end{pmatrix}$$

Next, the CPU 601 determines whether a highest reached point of the contour of the patient 8, of all of the trajectories calculated in the processing at step S14, exceeds the height limit (step S16). When it is determined that the highest reached point does not exceed the height limit (no at step S16), the CPU 601 performs the movement of the top surface plate 16a toward the target coordinates (step S17). When it is determined that the highest reached point exceeds the height limit (yes at step S16), the CPU 601 decreases a drive speed of the Z axis such that the highest point of the contour of the patient 8 is below the height limit (step S15). An example of the processing at step S15 is described below.

The CPU 601 finds a point for which the value on the Z axis is largest, among the points exceeding the Z axis limit. Next, the CPU 601 resets a Z axis speed Vz using the following Expression:

$Vz\_\text{new} = Vz\_\text{old} \times (Z \text{ axis limit value} - Z \text{ axis departure position})/(\text{value exceeding } Z \text{ axis limit} - Z \text{ axis departure position})$ Next, the CPU 601 verifies that the point exceeding the Z axis limit falls within the range of the limit, at the newly set Z axis speed Vz (step S16). When the point exists that does not fall within the limit (yes at step S16), the CPU 601 further resets the Z axis speed Vz using the above Expression (step S15), and using that, once more verifies the points exceeding the Z axis limit that have not yet been verified (step S16). Note that the speed for the Z axis is the speed of the second YZ axis motor 626, and is therefore not matched with the speed of the Z axis, and thus, a three-dimensional trace is once more performed for this determination. However, since the speed is definitely changed in the direction of becoming slower, there is no need to re-determine the point once determined to be exceeding the Z axis limit. When the operation at step S17 is complete, the processing ends.

As described above, in the present embodiment, the three-dimensional data of the contour of the patient 8 can be easily obtained by three-dimensionally reconfiguring the images from the plurality of optical cameras. Further, the CPU 601 of the control unit 60 can limit the movable range of the top surface plate 16a by performing the calculation such that the three-dimensional data of the contour of the patient 8 does not enter into the prohibited area of the neutron beam irradiation port 14o and the like due to the movement of the top surface plate 16a. Thus, before the irradiation port 14o comes into contact with the body of the patient 8, by the software simulation, the movable range of the top surface plate 16a can be changed in advance such that the three-dimensional data of the contour of the patient 8 does not enter into the prohibited area of the irradiation port 14o and the like. As a result, the contact between the patient 8 and the irradiation port 14o can be avoided.

Above, the preferable embodiment of the present invention is described in detail with reference to the drawings, but the present invention is not limited to the above embodiment, and may be implemented in other modes.

<Emergency Shutdown Processing>

Figure 21:
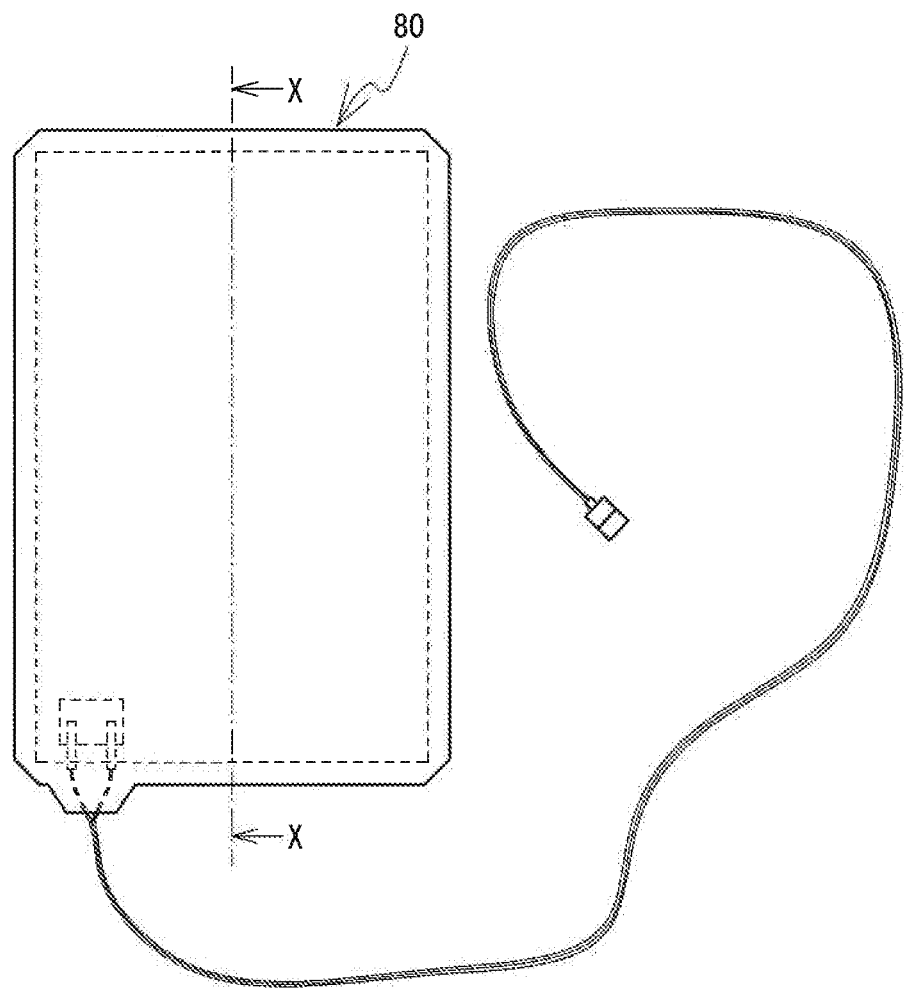
FIG. 21 is a plan view of a pressure sensor 80.
Figure 22:
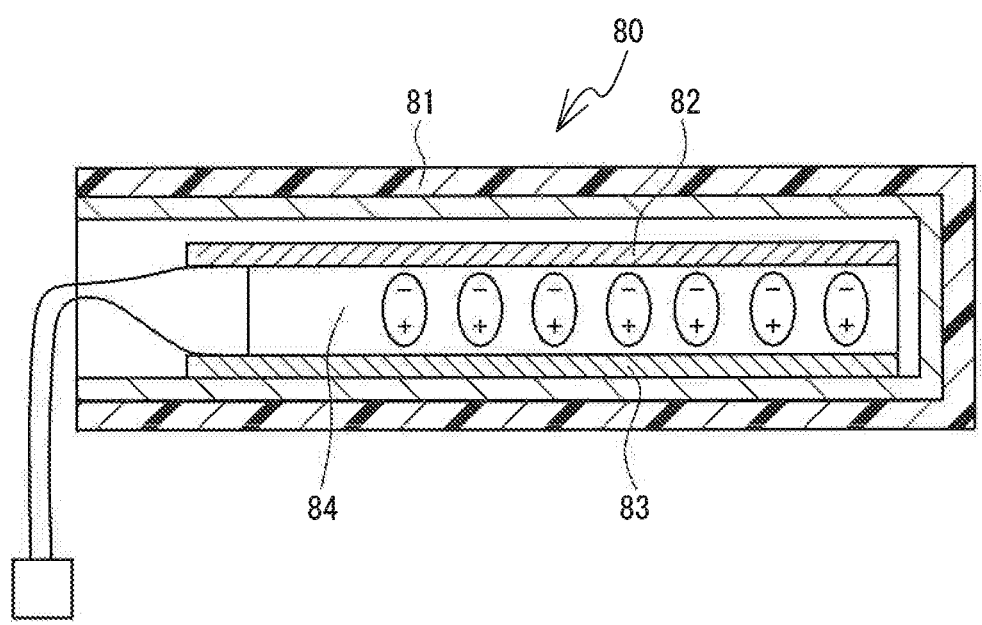
FIG. 22 is a cross-sectional view of the pressure sensor 80 in the direction of arrows on a line X-X shown in FIG. 21.

For example, in the above-described embodiment, the collision avoidance processing is realized by the simulation of the trajectory of the three-dimensional data of the contour of the surface of the body of the patient 8, but as shown in FIG. 21 and FIG. 22, emergency shutdown processing may be performed using a pressure sensor 80, which is an example of a proximity sensor. Specifically, the contact between the irradiation port 14o and the patient 8 may be detected using the pressure sensor 80 that physically detects the contact of the neutron beam irradiation port 14o, and the movement of the top surface plate 16a may be stopped as an emergency before an injury is incurred to the patient 8. The following requirements are necessary as specification requirements of the pressure sensor 80. In order to reduce secondary exposure caused by the radioactivation of materials, the main body of the pressure sensor 80 is formed of an organic material configured by elements with a low relative atomic mass. In order to avoid defects such as embrittlement, desensitization, electrical failure and the like caused by the neutron beams, a simple structure as possible is adopted. Due to the risks involved in the above two requirements, disposable use is assumed, and manufacturing costs are commensurate with this. Note that the arrangement of the pressure sensor 80 is on the surface of the body of the patient 8 in the vicinity of the neutron beam irradiation port 14o.

As an example of the pressure sensor 80 that satisfies the above-described requirements, a polyolefin piezoelectric film sensor may be used. As shown in FIG. 21, the pressure sensor 80 is rectangular in a plan view, and a cable extends from one end thereof and can be connected to the control unit 60. As shown by a cross-section in FIG. 22, the outer peripheral surface of the pressure sensor 80 is covered by an insulating laminate 81, and an anode 82 and a cathode 83 are provided in the interior of the pressure sensor 80. A film 84 made of a high polymer material that is polarized by pressure is sandwiched between the anode 82 and the cathode 83. An example of the high polymer material film 84 is a polyolefin piezoelectric film. The pressure sensor 80 has an extremely simple structure in which the high polymer material film 84 that is polarized by pressure is sandwiched between metallic foil that forms electrodes (the anode 82 and the cathode 83), and thus, a high degree of freedom is obtained with respect to the dimensions and the shape of the sensor. As a feature of a signal output of this pressure sensor 80, when the pressure applied to the sensor surface changes, a positive voltage is generated during compression, and a negative voltage is generated during release. If there is no change in the pressure applied to this voltage, since the voltage is attenuated by a time constant within one second, the pressure change resulting from contact can be detected regardless of the shape of the pressure sensor 80, which is adhered so as to follow the body of the patient.

As the emergency stop processing of the top surface plate 16a, by calculating an integrated value of the voltage within the latest second, a contact detection performance that is stable with respect to noise can be obtained. A function is installed that stops the movement when the integrated value exceeds a threshold value, and, in an operation verification test, it was verified that the emergency stop processing was activated at a sufficiently light force (approximately 0.5 kg×1 cm$^2$) before an injury was incurred, without reacting when a contact is simply made. The pressure sensor 80 using the polyolefin piezoelectric film as described above can reduce the secondary exposure caused by the radioactivation of materials, and, since it has a simple structure, can avoid defects such as embrittlement, desensitization, electrical failure and the like caused by the neutron beams. Further, material costs are cheap, and disposable use is possible. Note that a sensor other than the pressure sensor 80 may be used as the proximity sensor. For example, at least one of a high frequency oscillation type sensor, an ultrasonic sensor, a microwave sensor, an infrared sensor, a laser sensor, a photoelectronic sensor, an electrostatic capacitance sensor, and a magnetic sensor may be used. In this case, the approach of the irradiation port 14o can be detected before the contact with the body of the patient 8.

In addition, in the above-described embodiment, the CPU 601 of the control unit 60 controls the position adjustment portion 62, but a CPU may also be provided in the position adjustment portion 62, and the CPU provided in the position adjustment portion 62 may control the position adjustment mechanism 34, the first angle adjustment mechanism 36, and the second angle adjustment mechanism 38. Further, the patient 8 contour data generation processing shown in FIG. 16 may be performed by a computer other than the CPU 601 of the control unit 60.

Further, in the above-described embodiment, the patient 8 is placed on the patient restraint/placement unit 22 in the state of facing upward, but the present invention is not limited to this example, and the patient 8 may be placed and restrained on the patient restraint/placement unit 22 in a recumbent position on his or her side, or lying face down. In the above-described embodiment, the three-dimensional diagnostic device 18 is provided with the self-propelling image capture unit 26 that captures the three-dimensional image while being moved in the one direction with respect to the base 24, but a three-dimensional diagnostic device used in the present invention need not necessarily be provided with a self-propelling image capture unit, and various three-dimensional diagnostic devices that detect the position of the affected part in the patient 8 can be used. Although not particularly referred to in the above-described embodiment, as the neutron beams used in the boron neutron capture therapy of the present invention, the neutron beams having a specific energy that are safe with respect to living organisms are preferably used. In addition, although not individually exemplified, various modifications can be applied to and realized insofar as they do not depart from the spirit and scope of the present invention.

Figure 20:
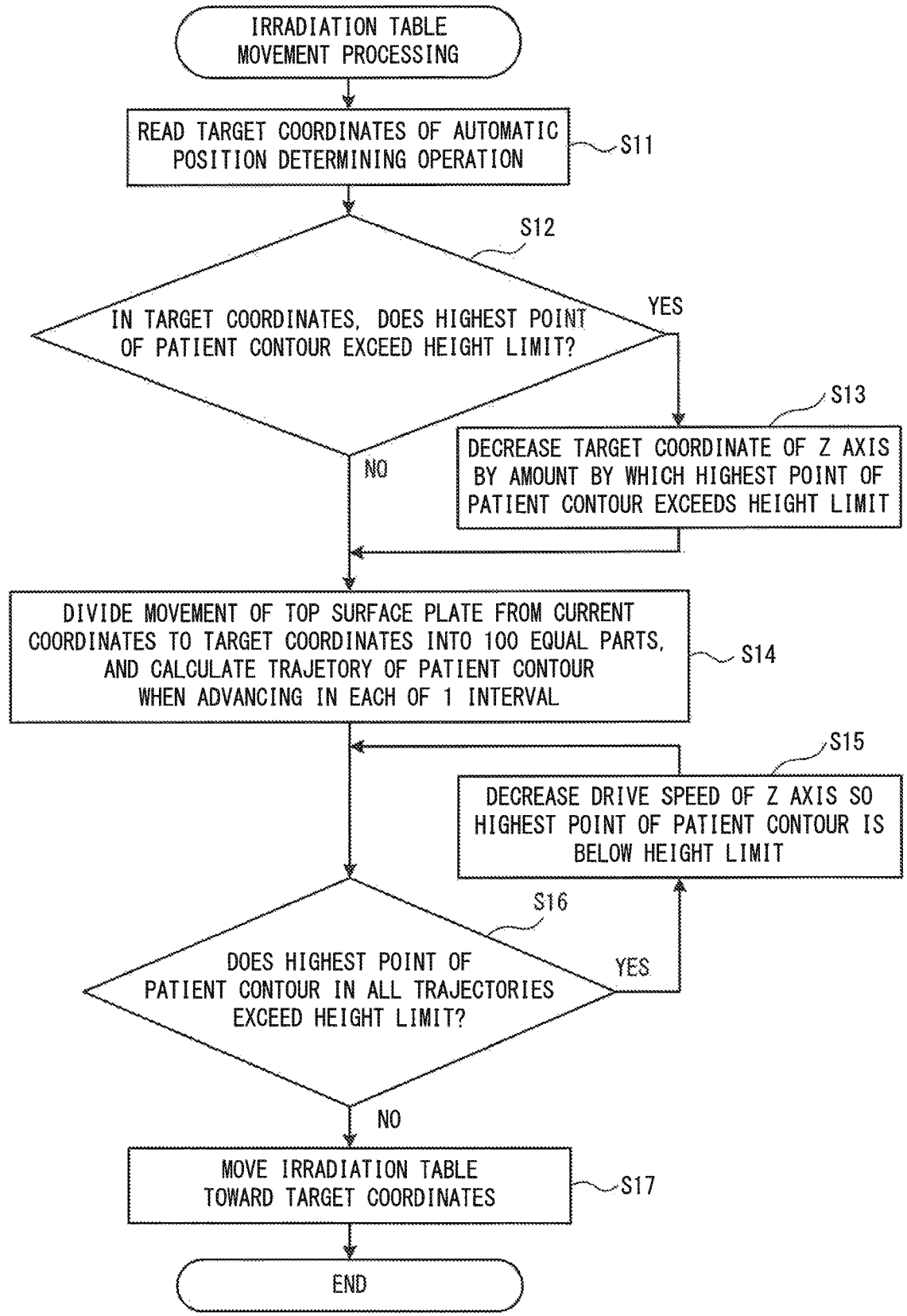
FIG. 20 is a flowchart of irradiation table movement processing.

Note that the processing at step S12 to step S15 of the flowchart shown in FIG. 20 performed by the CPU 601 is an example of "collision avoidance processing" of the present invention.

What is claimed is:

1. A boron neutron capture therapy system that is provided with a neutron beam irradiation device inside a room covered with neutron beam shielding, and that performs treatment by irradiating neutron beams onto an affected part, into which boron compounds have been injected, of a patient, using the neutron beam irradiation device, the boron neutron capture therapy system comprising:
- a patient restraint/placement portion configured to restrain the patient in a state of being placed on the patient restraint/placement portion;
- a three-dimensional diagnostic device configured to detect a position of the affected part in the patient;
- an irradiation table whose position is determined with respect to the neutron beam irradiation device;
- a position adjustment mechanism configured to change a position of the irradiation table with respect to an irradiation port of the neutron beam irradiation device, in relation to each of directions of three axes that are mutually orthogonal; and
- a control unit configured to align a position of the affected part in the patient detected by the three-dimensional diagnostic device with a position of neutron beams irradiated from the neutron beam irradiation device by changing, using the position adjustment mechanism, a position relating to each of the directions of the three axes of the irradiation table onto which the patient restraint/placement portion has been transferred, and configured to move the affected part as close as possible to the irradiation port, wherein
the control unit, using movement of the irradiation table, performs collision avoidance processing that changes the movement of the irradiation table before the patient restrained on the patient restraint/placement portion receives injury by colliding with the irradiation port.

2. The boron neutron capture therapy system according to claim 1, wherein
the control unit three-dimensionally measures a shape of a contour of the body of the patient restrained on the patient restraint/placement portion, estimates a spatial position of the contour of the body according to the movement of the irradiation table, and performs the collision avoidance processing.

3. The boron neutron capture therapy system according to claim 1, further comprising:
a proximity sensor configured to detect contact of the patient with the irradiation port,
wherein
the control unit performs emergency stop processing that stops the movement of the irradiation table as a result of an output of the proximity sensor.

4. The boron neutron capture therapy system according to claim 3, wherein
at least one of a pressure sensor, an ultrasonic sensor, a microwave sensor, an infrared sensor, a laser sensor, a photoelectronic sensor, an electrostatic capacitance sensor, and a magnetic sensor is used as the proximity sensor.

5. The boron neutron capture therapy system according to claim 3, wherein
a polyolefin piezoelectric film sensor is used as the proximity sensor.

6. The boron neutron capture therapy system according to claim 1, further comprising:
a position adjustment portion configured to, at a time of the detection of the position of the affected part using the three-dimensional diagnostic device, align the position of the affected part in the patient detected by the three-dimensional diagnostic device with the position of the neutron beams irradiated from the neutron beam irradiation device, by changing, using the position adjustment mechanism, the position of the irradiation table onto which the patient restraint/placement unit has been transferred in each of the directions of the three axes, on the basis of a mark that corresponds to positional coordinates relating to the detection and that is affixed to the patient placed and restrained on the patient restraint/placement unit.

7. The boron neutron capture therapy system according to claim 1, further comprising:
- a first angle adjustment mechanism configured to change an angle of the irradiation table with respect to an irradiation direction of the neutron beams, around an axis parallel to one axis of the three axes; and
- a second angle adjustment mechanism configured to change an angle of the irradiation table with respect to the irradiation direction of the neutron beams, around an axis parallel to another axis of the three axes that is different from the one axis.

8. The boron neutron capture therapy system according to claim 1, wherein
an engagement structure that is caused to be mutually engaged and is provided on each of portions of the patient restraint/placement unit and the irradiation table that face each other when the patient restraint/placement unit is transferred onto the irradiation table.

9. The boron neutron capture therapy system according to claim 6, wherein
the three-dimensional diagnostic device is a device configured to capture an image of the inside of the body of the patient, and
as a material of the mark, a material is used that allows sufficient distinction between a main material of the patient restraint/placement unit and the mark in the image captured by the three-dimensional diagnostic device.

10. The boron neutron capture therapy system according to claim 1, further comprising:
a transfer device configured to transfer the patient restraint/placement unit on which the patient is placed and restrained between the three-dimensional diagnostic device and the irradiation table; and,
a conveyance device, as the transfer device, configured to convey the patient restraint/placement unit while the patient restraint/placement unit is placed thereon,
wherein
the conveyance device includes
a holding portion configured to hold the patient restraint/placement unit and to be removable by being pulled out after the patient restraint/placement unit is transferred to one of the three-dimensional diagnostic device and the irradiation table, and
the patient restraint/placement unit on which the patient is restrained is transferred between the conveyance device and one of the three-dimensional diagnostic device and the irradiation table, using one of a raising/lowering mechanism provided in the conveyance device, a raising/lowering mechanism provided in the three-dimensional diagnostic device, and the position adjustment mechanism.

11. The boron neutron capture therapy system according to claim 7, further comprising:
a position display portion configured to perform display to verify that a position of the affected part in the patient detected by the three-dimensional diagnostic device is sufficiently aligned with respect to a position of the neutron beams irradiated from the neutron beam irradiation device; and a position adjustment portion configured to perform, on the basis of the display by the position display portion, adjustment using at least one of the position adjustment mechanism, the first angle adjustment mechanism, and the second angle adjustment mechanism such that an error in the position of the affected part in the patient detected by the three-dimensional diagnostic device with respect to the position of the neutron beams irradiated from the neutron beam irradiation device is within a prescribed permissible range.

12. The boron neutron capture therapy system according to claim 11, wherein the position display portion performs the display to verify that an imaging reference point of the image by the three-dimensional diagnostic device is sufficiently aligned with a coordinate system corresponding to the directions of the three axes, and the position adjustment portion performs the adjustment, on the basis of the display by the position display portion, such that an error of the imaging reference point of the image by the three-dimensional diagnostic device with respect to the coordinate system corresponding to the directions of the three axes of the irradiation table is within a prescribed permissible range.

* * * * *